(12) United States Patent
Wagner et al.

(10) Patent No.: US 7,767,455 B2
(45) Date of Patent: Aug. 3, 2010

(54) NUCLEUS EXPORT REPORTER SYSTEM

(75) Inventors: Ralf Wagner, Regensburg (DE); Marcus Graf, Regensburg (DE)

(73) Assignee: Geneart GmbH, Regensburg (DE)

( * ) Notice: Subject to any disclaimer, the term of this patent is extended or adjusted under 35 U.S.C. 154(b) by 818 days.

(21) Appl. No.: 10/415,483

(22) PCT Filed: Oct. 30, 2001

(86) PCT No.: PCT/EP01/12534

§ 371 (c)(1), (2), (4) Date: Oct. 21, 2003

(87) PCT Pub. No.: WO02/36791

PCT Pub. Date: May 10, 2002

(65) Prior Publication Data

US 2004/0087012 A1 May 6, 2004

(30) Foreign Application Priority Data

Oct. 30, 2000 (DE) ............................ 100 53 781

(51) Int. Cl.
 *C12N 15/00* (2006.01)
(52) U.S. Cl. .................................................. 435/455
(58) Field of Classification Search .................... None
See application file for complete search history.

(56) References Cited

FOREIGN PATENT DOCUMENTS

| WO | WO 97 48370 A | 12/1997 |
|----|---------------|---------|
| WO | WO 98 17309 A | 4/1998 |
| WO | WO 99 02694 A | 1/1999 |
| WO | WO 99 14310 A | 3/1999 |
| WO | WO9914310 | * 3/1999 |

OTHER PUBLICATIONS

Haas et. al. (1996) Current Biology vol. 6 No. 3 :315-324.*
Xu et al.(1997) Molecular and Cellular Biology vol. 17 (8) pp. 4611-4621.*
Kotsopoulou et al. (2000) Journal of virology vol. 74 (10) pp. 4839-4852.*
Muller et al. (1992) J. Mol. Biol. 226: 721-733.*
Gutierrez et al. (1999) Trends in Plant Science vol. 4 No. 11. pp. 429-438.*
F.J. Van Hemert et al., "The Tendency of Lentiviral Opening Reading Frames to Become A-Rich: Constraints Imposed by Viral Genome Organization and Cellular tRNA Availability"; Journal of Molecular Evolution, Bd. 41, Nr. 2, 1995, pp. 132-140, XP008014811.
J. Haas et al., "Codon Usage Limitation in the Expression of HIV-1 Envelope Glycoprotein"; Current Biology, Current Science, GB, Bd. 6, Nr. 3, Mar. 1, 1996, pp. 315-324, XP000619599.
E. Kotsopoulou et al., "A Rev-independent human immunodeficiency virus type 1 (HIV-1) based vector that exploits a codon-optimized HIV-1 gag-pol gene", Journal of Virology, The American Society for Microbiology, US, Bd. 74, Nr. 10, May 2000, pp. 4839-4852, XP002140792.
V.W. Pollard et al., "The HIV-1 Rev protein", Annual Review of Microbiology 1998 United States, Bd. 52, 1998, pp. 491-532, XP008014663.
X. Lu et al., "U1 small nuclear RNA plays a direct role in the formation of a rev-regulated human immunodeficiency virus env mRNA that remains unspliced", Proceedings of the National Academy of Sciences of the United States of America 1990 United States, Bd. 87, Nr. 19, 1990, pp. 7598-7602, XP002233598.
M. Graf et al., "Concerted Action of Multiple CIS-Acting Sequences is Required for Rev Dependence of Late Human Immunodeficiency Virus Type 1 Gene Expression", Journal of Virology, The American Society for Microbiology, US, Bd. 74, Nr. 22, Nov. 2000, pp. 10822-10826, XP000971716.
R. Wagner et al., "Rev-Independent Expression of Synthetic gag-pol genes of Human Immunodeficiency Virus Type 1 and Simian Immunodeficiency Virus: Implications for the Safety of Lentiviral Vectors", Human Gene Therapy, XX, XX, Bd. 11, Nr. 17, Nov. 20, 2000, pp. 2403-2413, XP000974656.
K. Boris-Lawrie et al., "Retroviral RNA elements integrate components of post-transcriptional gene expression", Life Sciences Oct. 26, 2001 United States, Bd. 69, Nr. 23, pp. 2697-2709, XP002233599.

* cited by examiner

*Primary Examiner*—Kenneth R. Horlick
*Assistant Examiner*—Suchira Pande
(74) *Attorney, Agent, or Firm*—Miller, White, Zelano & Branigan, P.C.

(57) ABSTRACT

The present invention relates to reporter systems for RNA export, methods for searching for molecules which influence RNA export, and a method, based on these methods, for detecting a viral infection.

21 Claims, 14 Drawing Sheets

Fig. 1

Comparison of hivGFP versus huGFP

```
  1 ATGGTAAGCAAAGGAGAAGAATTATTTACAGGAGTAGTACCAATATTAGT  50
    ||||  ||||| || || ||  | || || || || || || ||  |  ||
  1 ATGGTGAGCAAGGGCGAGGAGCTGTTCACCGGGGTGGTGCCCATCCTGGT  50

51 AGAATTAGACGGtGACGTAAATGGACATAAATTTAGCGTAAGCGGAGAAG 100
    ||  | |||||| |||||||| || || || || ||||| ||| || |
 51 CGAGCTGGACGGCGACGTAAACGGCCACAAGTTCAGCGTGTCCGGCGAGG 100

101 GAGAAGGtGACGCAACATATGGAAAATTAACATTAAAATTTATATGTACA 150
    | || || || || || || || || || ||  | || | || || || ||
101 GCGAGGGCGATGCCACCTACGGCAAGCTGACCCTGAAGTTCATCTGCACC 150

151 ACAGGAAAATTACCAGTACCcTGGCCAACATTAGTAACAACATTTACATA 200
    || || ||  | || || |||||||| ||  | || || || || || ||
151 ACCGGCAAGCTGCCCGTGCCCTGGCCCACCCTCGTGACCACCTTCACCTA 200

201 TGGAGTACAATGTTTTAGCAGATATCCAGACCATATGAAACAACATGACT 250
    || || || || || || ||| | || || |||| ||||| || || ||||
201 CGGCGTGCAGTGCTTCAGCCGCTACCCCGACCACATGAAGCAGCACGACT 250

251 TTTTTAAAAGCGCAATGCCAGAAGGATATGTACAAGAAAGAACAATATTT 300
    |  || ||   ||| ||||| ||||| || || || ||  | || || ||
251 TCTTCAAGTCCGCCATGCCCGAAGGCTACGTCCAGGAGCGCACCATCTTC 300

301 TTTAAAGACGACGGAAATTATAAAACAAGAGCAGAAGTAAAATTTGAAGG 350
    || || |||||||| || || || || || | || || || || || ||
301 TTCAAGGACGACGGCAACTACAAGACCCGCGCCGAGGTGAAGTTCGAGGG 350

351 AGACACATTAGTAAATAGAATAGAATTAAAAGGAATAGACTTTAAAGAgG 400
    ||||| | || ||  | || ||  | || || ||||| ||  | ||||
351 CGACACCCTGGTGAACCGCATCGAGCTGAAGGGCATCGACTTCAAGGAGG 400

401 ACGGAAATATATTAGGACATAAATTAGAATATAATTATAATAGCCATAAT 450
    ||||| || || || |  | || ||  | || || || || || || ||
401 ACGGCAACATCCTGGGGCACAAGCTGGAGTACAACTACAACAGCCACAAC 450

451 GTATATATAATGGCAGACAAACAAAAAATGGAATAAAAGTAAATTTTAA 500
    || ||||| |||| |||||| ||| || || || || || || || ||
451 GTCTATATCATGGCCGACAAGCAGAAGAACGGCATCAAGGTGAACTTCAA 500

501 AATAAGACATAATATAGAgGACGGAAGCGTACAATTAGCAGACCATTATC 550
    ||  | || || || || ||||||||  ||| ||  | || |||| || |
501 GATCCGCCACAACATCGAGGACGGCAGCGTGCAGCTCGCCGACCACTACC 550

551 AACAAAATACACCAATAGGtGACGGACCAGTATTATTACCAGACAATCAT 600
    | || || || ||  | || |||||  |  | || |||| || || ||
551 AGCAGAACACCCCCATCGGCGACGGCCCCGTGCTGCTGCCCGACAACCAC 600

601 TATTTAAGCACACAAAGCGCATTAAGCAAAGACCCAAATGAAAAAAGAGA 650
    || | |||||| ||    |||  | |||||||||||||| || || || |
601 TACCTGAGCACCCAGTCCGCCCTGAGCAAAGACCCCAACGAGAAGCGCGA 650
```

Fig.1 continued

```
651 CCATATGGTATTATTAGAATTTGTAACAGCAGCAGGAATAACATTAGGAA 700
    || |||||  |  | || || || || || || || || || |  ||| |
651 TCACATGGTCCTGCTGGAGTTCGTGACCGCCGCCGGGATCACTCTCGGCA 700

701 TGGACGAATTATATAAATAA 720
    |||||||  |  || || |||
701 TGGACGAGCTGTACAAGTAA 720
```

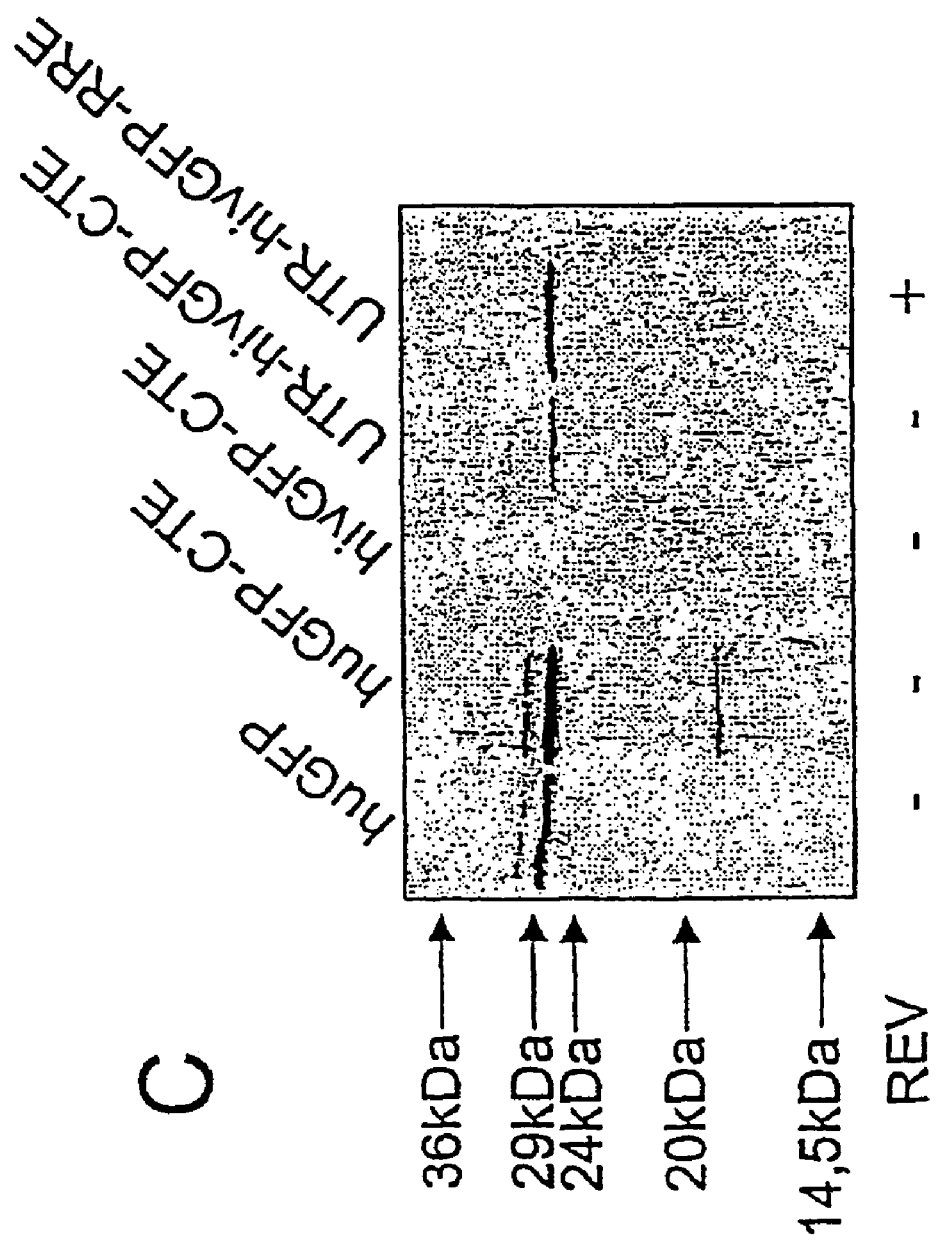

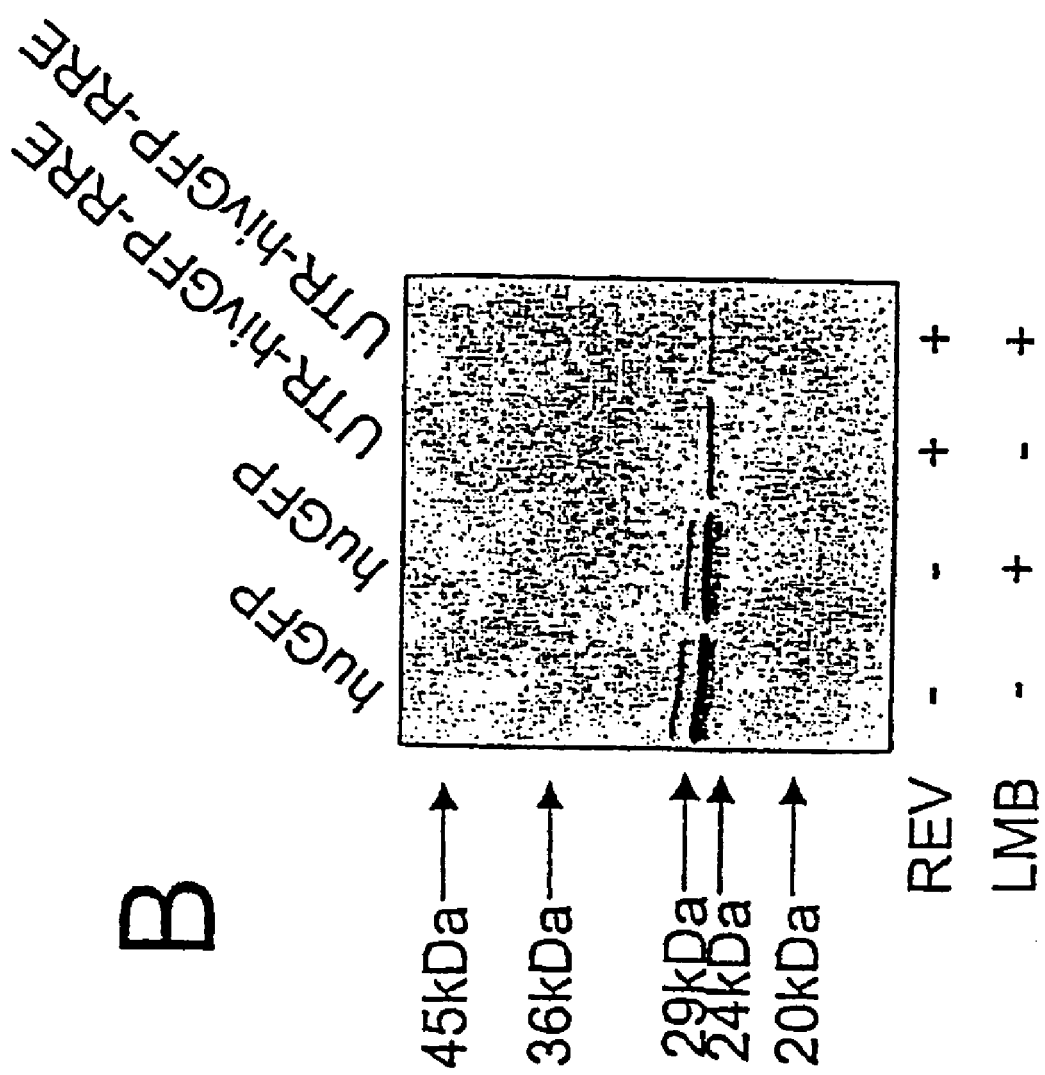

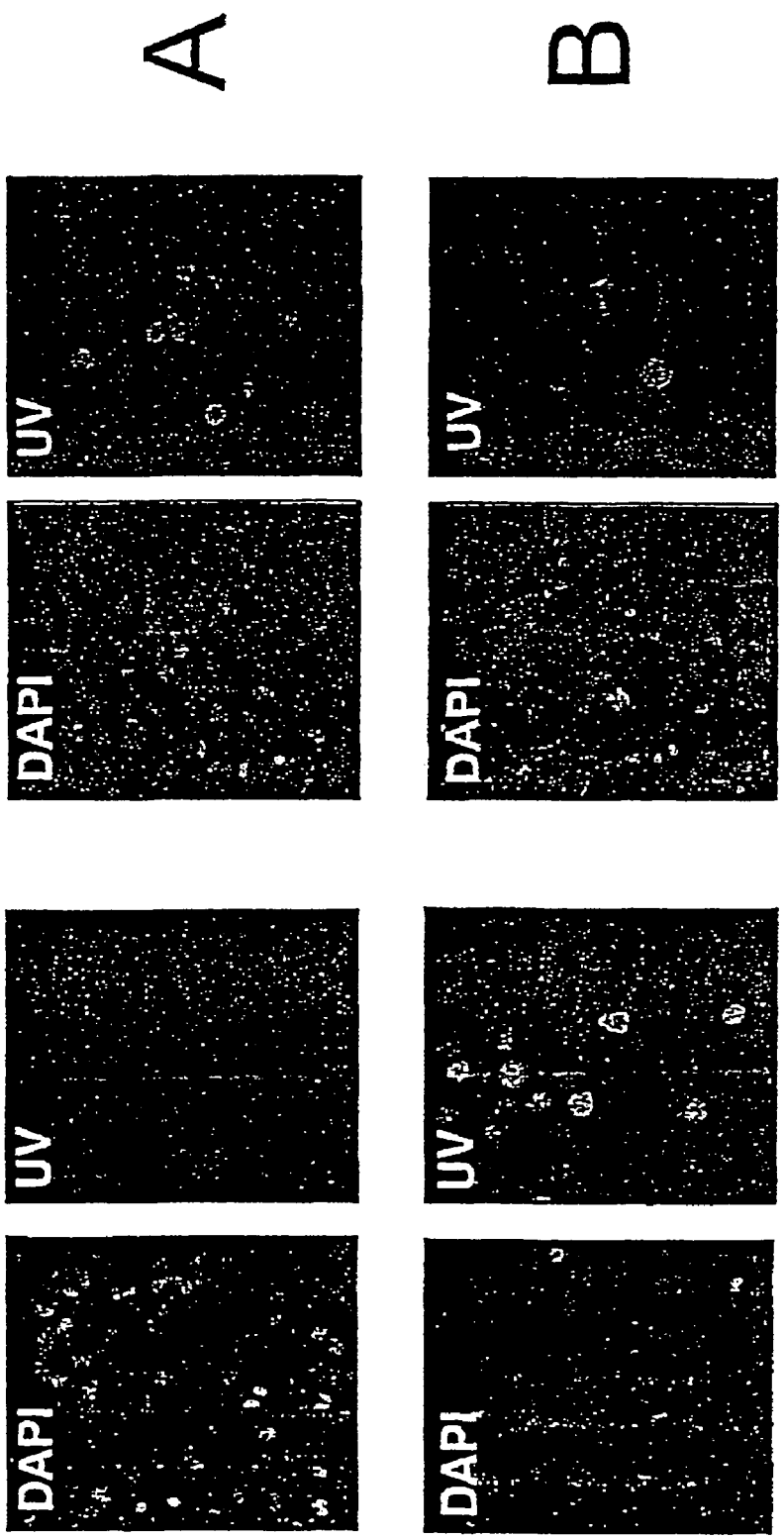

NUCLEUS EXPORT REPORTER SYSTEM

The present invention relates to reporter systems which permit the identification of proteins, signal sequences and/or active substance candidates which regulate the export of RNAs (ribonucleic acids) and, in particular, viral RNAs from the cell nucleus of eukaryotic cells.

A wide variety of viruses depend on active export of their incompletely spliced transcripts from the cell nucleus of the infected host cell. This can either take place by use of an RNA signal in cis within the viral transcripts (constitutive transport elements), or takes place with the aid of viral proteins. Cis-active transport elements are used for example from MPMV-CTE (Mason-Pfizer monkey virus constitutive transport element), SRV-CTE (simian retrovirus constitutive transport element), hepatitis B virus PRE (posttranscriptional regulatory element) and HSV (herpes simplex virus) (within the TK (thymidine kinase) gene). These RNA elements recruit cellular factors and export pathways in order to enable nuclear export of the viral transcripts. An alternative possibility is for nuclear export also to be mediated by an export factor which specifically binds to a target sequence within the viral transcripts and transports the latter into the cytoplasm through interaction with cellular factors. Thus, for example, Ad-5 transcripts are exported with the aid of the 34K and E4orf6 proteins, EBV (Epstein-Barr virus) transcripts with the aid of the EB2 protein, herpes-virus saimiri transcripts with the aid of the ORF 57 gene product, HSV (herpes simplex virus) transcripts with the aid of the ICP 27 protein, HTLV-I and II (human T-cell leukemia virus I and II) transcripts with the aid of the Rex proteins, EIAV (equine infectious anemia virus), SIV (simian immunodeficiency virus) and HIV-1 and HIV-2 (human immunodeficiency virus 1 and 2) transcripts with the aid of the Rev proteins.

Nuclear export which has been investigated best is that of late HIV-1 transcripts mediated by HIV-1 Rev. Like all lentiviruses HIV-1 depends on a plurality of genes being activated from only one proviral template and being expressed in a fixed time sequence. Different genes are generated from a primary transcript which is only ~9 kB in size by alternative splicing events and other regulatory mechanisms taking place at the RNA level. These viral transcripts can be divided into 3 classes on the basis of their size: ~9 kB unspliced (gag, pol), ~4 kB singly spliced (env, vif, vpr, vpu) and ~2 kB multiply spliced (rev, tat, nef) RNAs.

Besides the occurrence of incompletely to multiply spliced transcripts, it is additionally possible to observe a time sequence in the expression of these different RNA species. Thus, only the multiply spliced ~2 kB RNAs, and their gene products Rev, Tat and Nef, are detectable in the early phase of replication in the cytoplasm of the infected cells. Only after a time lag do the unspliced (~9 kB) and singly (~4 kB) spliced transcripts and their gene products Gag, Pol and Env then also appear therein. However, the singly and unspliced transcripts can never be detected in the cytoplasm of cells infected with viral mutants lacking an active Rev protein. The unspliced and singly spliced transcripts then accumulate in the nucleus, and the late structural proteins (Gag, Env) and enzymes (Pol) translated from them cannot be formed. The viral Rev protein is thus essentially involved in the time-regulated expression of the viral genes.

HIV-1 Rev, just like the RNA transport molecules mentioned above, are shuttle proteins which transport viral RNAs via the interaction with an RNA target sequence located within viral transcripts the latter out of the nucleus into the cytoplasm. Thus, HIV-1 Rev binds specifically in the nucleus to its RNA target structure RRE, the Rev-responsive element (see FIG. 5 A/B). This region, which is 351 nucleotides (Nt) long, is located within the Env reading frame and is thus a constituent of all unspliced and singly spliced transcripts. This ribonucleoprotein (RNP) complex is subsequently exported out of the cell nucleus via interaction with cellular factors. A leucine-rich sequence located at the C terminus is necessary for this and, as nuclear export sequence (NES), mediates nuclear translocation of the Rev protein through use of cellular mechanisms (Pollard and Malim, 1998).

The reason why the late transcripts remain in the nucleus in the absence of Rev, which is a necessary condition for the Rev-dependence and thus the time-regulated expression of Gag, Pol and Env, is still controversial. In principle there are two main alternative ideas about the nuclear retention of late transcripts.

It is assumed that a cellular transcript can leave the cell nucleus only when the splicing process is entirely complete, or all active splice sites have been deleted from the primary transcript. The late viral transcripts are intron-containing, only incompletely spliced pre-mRNAs which are transported into the cytoplasm with the aid of Rev and RRE. The influence of the cellular splicing machinery on the nuclear retention of the late transcripts was therefore investigated at an early date (Mikaelian et al., 1996; Kjems et al., 1991; Kjems and Sharp, 1993; Chang and Sharp, 1989; Powell et al., 1997; Lu et al., 1990; O'Reilly et al., 1995). The presence of splice sites differing in activity appears to make the splicing process only suboptimal in the case of HIV-1 transcripts. Several groups have therefore hypothesized that Rev makes it possible for transcripts which are retained within the splicing machinery through the formation of inefficient splicing complexes to be exported.

However, contrary to this it has been possible to show that expression of the late HIV-1 genes such as, for example, Env remains repressed even in the absence of active splice sites, and thus the influence of the splicing machinery appears to be more indirect (Nasioulas et al., 1994). This is why so-called inhibitory sequences (INS) or cis-active repressor elements (CRS) within the reading frames, which adversely influence expression, have been postulated (Nasioulas et al., 1994; Olsen et al., 1992; Schwartz et al., 1992b; Maldarelli et al., 1991). However, these repressor sequences which are located inside the coding mRNA have no common sequence motif like, for example, the AUUUA instability motif inside the 3'-UTR of the unstable GM-CSF mRNA (Chen and Shyu, 1995), but are conspicuous only by their high A/U content throughout. Thus, fusion of the postulated INS-containing fragments from reading frames of late genes (such as Gag and Env) to a CAT reporter system resulted in a reduced reporter activity (Cochrane et al., 1991; Rosen et al., 1988; Schwartz et al., 1992b). It was possible to abolish again in part this reduction in the expression of Gag and Pol in part by multiple silent point mutations within the wobble positions (Schwartz et al., 1992a; Schneider et al., 1997). The unspliced and singly spliced HIV-1 mRNAs thus appear to have cis-active repressor elements which are either deleted by multiple splicing or overcome by a Rev/RRE-mediated nuclear export.

There is great medical interest in molecules which modulate, in particular inhibit, the export of RNA, in particular viral RNA, from the cell nucleus. For example, HIV-1 Rev is an essential factor during replication of HI viruses both in cell culture and in vivo. (Feinberg, Jarrett, 1986; Iversen, Shpaer, 1995; Sodroski, Goh, 1986). This makes Rev an attractive target for therapeutic agents with antiviral activity.

Rev-sensitive reporter systems can be used for testing active substances which suppress a Rev function and thus prevent productive replication of HIV-1. A wide variety of systems has been used to date for evaluating the Rev-dependent HIV-1 gene expression. These extend from mutated provirus constructs (Borg et al., 1997; Malim and Cullen, 1993) via chimeric Rev-sensitive β-globin genes (Chang and Sharp, 1989; Mikaelian et al., 1996) to subgenetic fragments fused to reporter genes (Schwartz et al., 1992a; Schwartz et al., 1992b).

However, the systems used to date are not suitable for the high-throughput testing (HTT) of therapeutic agents with a Rev-inhibiting effect, or for the isolation of specific inhibitors of the Rev function from a randomized gene library: working with viral systems or provirus constructs capable of replication requires S3 safety laboratories, and elaborate and costly (p24 capture ELISA) detection methods which do not permit HTT per se or make it unattractive. Complex Rev-dependent β-globin reporter systems are suitable only for basic research, and require special, demanding laboratory methods (Northern blot, RNA protection assay), which likewise preclude HTT. Reporter systems based on a specific enzymatic reaction for detecting Rev-sensitive gene expression permit HTT at least in some cases. Thus, it has been possible to convert expression of the chloramphenicol acetyltransferase (CAT) gene into Rev dependence by placing the CAT reading frame together with the RRE region inside an intron sequence (Luo et al., 1994; Iacampo, Cochrane, 1996; Hope, Huang, 1990), This reporter construct (pDM128 and derivatives) has a number of disadvantages, however:

(a) The assay cannot be used on a single cell basis. Thus cells cannot be separated by FACS but must necessarily be lysed for analysis.
(b) Simple, easily automatable, optical testing of a Rev action is not possible.
(c) Unspliced CAT RNAs can be detected in the cytoplasm of cells transfected with pDM128 even in the absence of Rev, i.e. a Rev dependence is incorrectly simulated in the assay even in the absence of Rev.
(d) The presence of an intact cellular splicing machinery is a precondition for the assay. Molecules which influence splicing processes are incorrectly classified as modulators of RNA export in the assay.

It was therefore an object of the present invention to provide a method for detecting RNA export from the cell nucleus of a eukaryotic cell which does not have the abovementioned disadvantages of the prior art.

This object is achieved by a method comprising the steps:
(a) provision of a nucleic acid which codes for a reporter protein and whose transcript is exported from the cell nucleus depending on the presence
  (i) of a cis-active RNA export signal in operative linkage with the nucleic acid and
  (ii) of a trans-active factor and, where appropriate,
  (iii) of a functional 5' splice donor in the absence of a functional 3' splice acceptor,
(b) introduction of the nucleic acid into the cell nucleus of the target cell so that it is present therein in operative linkage with a transcription control sequence, and that on transcription of the nucleic acid there is generation of a transcript in which the segment of the transcript coding for the reporter protein cannot be subjected to any splicing process,
(c) transcription of the nucleic acid and
(d) determination of whether the resulting transcript is exported from the cell nucleus.

The presence of the 5' splice donor must not lead to a splicing event being possible as in the case of the constructs of Lu et al. Accordingly, the 5' splice donor must not be confronted by a 3' splice acceptor or at least any efficiently utilized splice acceptor.

The cis-active RNA export signal may be a previously known RNA export signal. In this case, the RNA export signal is preferably positioned in relation to the reporter gene in analogy to the natural occurrence of the export signal. Thus, for example, in the case of the Rev-responsive element of HIV-1 the signal is cloned downstream of the reporter gene. Conversely, the export signals of adenoviruses are preferably disposed upstream of the reporter gene.

The method of the invention is suitable for the identification of unknown RNA export signals. For this purpose, the reporter gene is operatively linked in the nucleic acid to a library of gene fragments, and constructs which make RNA export possible are sought. The gene fragment library preferably comprises genes or gene fragments from donor organisms or viruses known to have efficient RNA export signals. If it is intended specifically to search for RNA export signals which require the presence of viral trans-acting factors, these must likewise be provided in the cell.

It is conversely possible, if a cis-active export signal is known and a trans-active factor is to be identified, to use a construct as described above to search for such a factor. In this case, the nucleic acid construct comprises both the reporter gene and the cis-active signal. It is then possible to use the reporter system described above to search in expression libraries for trans-active factors. The trans-active factors are preferably viral adaptor molecules which mediate an interaction with the cellular RNA export machinery, but they may also be cellular molecules. Such a trans-active factor includes for the purposes of this application both a single protein and a protein complex.

If all the cis- and trans-acting factors necessary for RNA export are provided, the system is suitable for identifying molecules which influence RNA export. The molecule which influences RNA export may be, for example,
(a) a small molecule, typically having a molecular mass of less than 2 000 Da,
(b) DNA or RNA, derivatives or mimetics thereof, which act at the nucleic acid level or interact with proteins involved in RNA export, or
(c) a peptide, a modified peptide, protein or modified protein which interacts with nucleic acids or interacts with proteins involved in RNA export.

An example of a small molecule as in (a) is leptomycin B, a known inhibitor of Rev activity. An example of a nucleic acid as in (b) are the known RRE decoys and an RNA intramer. An example of a protein as in (c) is the transdominant-negative Rev mutant RevM10. It is possible in particular for the nucleic acids to be derived from a gene library or for the proteins to be gene products of the genes of a gene library. In these cases, the advantage of the system of the invention, of dispensing with lysis or fixation of the cells, is very particularly evident.

The activity of leptomycin B and of the transdominant-negative Rev mutant RevM10 were detectable with the reporter system of the invention (with hivGFP as reporter protein). The produced Rev-sensitive reporter system is thus suitable for detecting inhibition of viral gene expression and thus as reporter system for identifying therapeutic agents with antiviral activity and acting on viral nuclear export.

A further substantial improvement of the reporter system of the invention compared with the previously disclosed CAT system is the avoidance of splicing processes. In the CAT system, RNA is exported into the cytoplasm in every case. Only in the presence of a trans-active factor such as, for example, Rev does the latter also contain an intron on which the reporter gene is encoded. By contrast, in the reporter system of the invention there is no need for a splicing event to take place. In the absence of cis- or/and trans-active signals, the RNA is just not exported into the cytoplasm in amounts which allow the accumulation of detectable amounts of RNA.

This can be achieved, for example, by RNA-destabilizing sequence motifs such as, for example, AUUUA which occurs in the RNA for GM-CSF, or preferably by a choice of codons which reduces the metabolic stability of the RNA. Constructs suitable for reporter systems of the invention can be generated for example by choosing the codon distribution like that occurring in viral exported RNA. A choice of codons to be used preferably in this connection is one like that used least frequently or second-least frequently in mammalian cells (Ausubel et al., 1994), even more preferably the choice of codons is adapted to that of late HIV-1 genes, and even more preferably table 1 is used for producing the Rev-dependent reading frame.

For example, the choice of codons of the constitutively expressing gene for green fluorescent protein (GFP) was adapted to the choice of codons like that to be found in late HIV-1 genes. For this purpose, the amino acid sequence of the GFP gene product was back-translated into a synthetic GFP-encoding reading frame using the HIV-1 Gag choice of codons. This reading frame, called hivGFP, was then constructed as fully synthetic reading frame using long oligonucleotides and a stepwise PCR. In addition, the authentic 5'-UTR of the Gag reading frame was put in front of the hivGFP reading frame, and the RRE was attached 3' and cloned into an expression vector. The produced hivGFP vector proved to be completely dependent on the presence of the Rev protein in the expression of the autofluorescent GFP. In the absence of the 5'-UTR, RRE or Rev it was not possible to detect any expression of the green fluorescent reporter. The initial GFP gene, which was adapted in its choice of codons to mammalian genes (huGFP), by contrast proved to be independent of Rev, RRE or the 5'-UTR in its expression.

However, instead of adapting the choice of codons as accurately as possible to the choice of codons of late HIV genes, it is also possible merely to increase the AT content. An AT content of >50% is preferably aimed at. Increasing the AT content or adapting the codon usage preferably takes place by silent mutations or by mutations which do not destroy the activity of the reporter protein. The choice of codons need not be adapted if the A/T content of said gene is already more than 50%. Genes with a codon usage differing from the wild type can be produced as indicated in the example for example from long oligonucleotides and with a stepwise PCR.

The reporter protein preferably used is a fluorescent protein, because of the particularly simple readability and the suitability for high-throughput tests. Examples of autofluorescent reporter proteins are the green fluorescent protein GFP, the blue fluorescent protein BFP, the red fluorescent protein RFP, the yellow fluorescent protein YFP, or derivatives of these autofluorescent proteins which display increased fluorescence, such as the enhanced green fluorescent protein eGFP, the enhanced blue fluorescent protein eBFP, the enhanced red fluorescent protein eRFP or the enhanced yellow fluorescent protein eYFP (Clontech).

Instead of using fluorescent proteins it is also possible to use other proteins as long as their activity is easily detectable. Examples are the gene for luciferase LUC, the gene for alkaline phosphatase AP, the gene for secretory alkaline phosphatase SEAP or the gene for choramphenicol acetyltransferase CAT.

Immunologically detectable proteins are likewise suitable as reporter proteins. It is sufficient for rapid immunological detection of the gene product, of parts of the gene product or of epitopes to be possible. A frequently used example is the influenzae Flag-tag.

Proteins capable of positive or negative selection are also suitable as reporter proteins. For example, the neomycin-resistance gene prevents a translation block caused by G418 and thus death of the cell. In HAT (hypoxanthine, aminopterin, thymidine) medium, in which de novo purine and pyrimidine biosynthesis is blocked, the activity of thymidine kinase is essential. Conversely, it is possible to select for cells deficient in thymidine kinase by propagating the cells in bromodeoxyuridine. Likewise, the enzymic activity of the herpes viral thymidine kinase (TK) brings about the death of TK-expressing cells in the presence of acyclovir. Further examples of markers capable of positive and negative selection are adenine phosphoribosyl transferase (APRT), hypoxanthine-guanine phosphoribosyl transferase (HGPRT), and dihydrofolate reductase (DHFR). Azaserine is used for positive, and 8-azaguanine for negative, selection for APRT and HGPRT. In the case of DHFR, methotrexate is used for selection for the marker, and [$^3$H]dUrd is used for selection against the marker. All the marker systems mentioned are described in detail by Kaufmann (Kaufmann, 1979).

Finally, the reporter gene may be a regulatory gene which, after its expression in a cell as molecular switching molecule, switches the expression of other genes on or off. An example of such a regulatory gene which can be used is a transcription factor.

In all methods in which it is not intended to search for a cis-active RNA export signal, the nucleic acid construct already contains a cis-active RNA export element.

This may be may be a so-called constitutive transport element. No viral proteins are necessary for the export for the nuclear export of RNAs which harbor such a constitutive transport element; the virus merely utilizes cellular mechanisms which are already present. Examples of such cis-active RNA export elements are MPMV CRE, RSV CTE or SRV CTE.

Many viral cis-active RNA export elements are, however, dependent on viral adaptor proteins which mediate the interaction with the cellular export machinery. In the case of HIV, the RRE (Rev responsive element) is used as cis-active RNA export element. This signal is recognized by the viral protein Rev which contains a leucine-rich sequence of hydrophobic amino acids which acts as nuclear export signal (NES). The Rev receptor in nuclear export is Crm1, which is also called exportin 1. Interaction of the Rev receptor with Crm1 can be impaired by leptomycin B. It is thought that the Rex/RxRRE system of HTLV-I and HTLV-II functions analogously to the Rev/RRE system of HIV-1, HIV-2 and SIV.

The RNA export signal for the RNA export systems described hereinbefore is preferably located downstream of the structural genes. However, it is also possible to use RNA export signals from viruses in which the RNA export signals are located upstream of the structural genes, as occurs for example in adenoviruses. In this case, the nuclear export sequence is preferably located upstream of the reporter gene in the RNA constructs too.

The invention further relates to a DNA sequence which codes for a reporter protein and is operatively linked to a cis-active RNA export element and, where appropriate, to a functional 5' splice donor in the absence of a functional 3' splice acceptor, where (a) the DNA sequence coding for the reporter protein is modified at the nucleic acid level compared with the wild-type sequence, (b) RNA export for the modified DNA sequence takes place dependent on the cis-active RNA export element, and
(c) essentially no RNA export for the wild-type DNA sequence takes place dependent on the cis-active RNA export element.

The wild type means in this connection either the wild type in the usual sense or else a gene which is optimized for expression in the corresponding host cell, such as, for example, "humanized GFP". The dependence of the modified reporter RNA on the cis-active RNA export element is achieved by the methods described above.

Transcription of the corresponding RNA sequence is controlled by a transcription control sequence. The transcription control sequence may comprise a constitutive or inducible promoter. Examples of constitutive promoters which can be used are viral promoters from CMV, SV 40 or from adenovirus or cellular promoters such as the actin promoter or cell type-specific promoters such as the MHCII promoter. Suitable inducible promoters are tetracycline-dependent promoters (Tet on/off system), heat shock promoters, metallothionein promoters or promoters which can be induced by glucocorticoids, such as the promoter in mouse mammary tumor virus (MMTV) LTR (Kaufmann, 1979). An appropriate polyadenylation signal is attached to the 3' end of the DNA for the polyadenylation of the RNA transcripts. The statements made above apply to the choice of the reporter protein and of the cis-active RNA export signal. It is appropriate in some circumstances to provide a trans-active factor and the reporter construct on the same plasmid.

The present invention further relates to eukaryotic cells, more preferably mammalian cells, most preferably human cells, which are transformed with a DNA construct as described above, where the DNA construct is present in a form capable of transcription. The DNA construct may for example exist episomally or be stably integrated into the chromosome. It is moreover possible for one or more copies to be present in the cell. If an RNA export sequence which is active only in the presence of a viral export factor is used, it is possible by transfection or infection of the cell with expression libraries to search for viral factors which interact with the RNA export sequence or act further downstream in the RNA export pathway, if such factors are not yet known. If the RNA export activity is successfully reconstituted, it must be possible to measure an increase in the expression of the Rev-dependent gene by at least 2.5-fold, preferably 5-fold, more preferably 8-fold or more.

If the factors are already known, they are preferably made available in the cell, usually in trans. The invention therefore relates to the production of stable cell lines which, besides the export construct described above, also harbor the gene for an additional viral export factor integrated chromosomally or episomally in them. It is possible to use according to the invention any eukaryotic cell in which the factors necessary for RNA export are present in concentrations which correspond approximately to the natural infection model. Except for the infection model described hereinafter, it is unnecessary for the cells to be permissive for replicative infection with the viral system to be investigated. Examples of eukaryotic cells which can be used are H1299 cells, HeLa cells, HEK cells (human embryonic kidney cells).

The viral export factor is preferably Rev from HIV-1, HIV-2, SIV and EIAV or Rex from HTLV-I and HTLV-II, or the 34K and E4orf6 proteins from adenoviruses, or EB2 proteins from EBV, or ORF 57 gene products from herpes virus saimiri, or ICP 27 proteins from HSV.

The present invention further relates to the production of stable cell lines which, besides the Rev-dependent gene, additionally comprise one or more constitutively expressing genes. It is possible by determining the rate of expression of these genes or the amount of the relevant protein products to distinguish whether an active substances to be tested specifically affects the expression dependent on the export factor provided in trans, or only generally blocks cellular expression. The reporter gene whose expression is regulated by the viral export factor, and the constitutively expressed protein must be detectable by different methods. If both proteins are fluorescent, they must therefore differ in the wavelength of the exciting light or in the wavelength of the emitted light. However, it is also possible to use other enzymatic methods or the recognition of another immunological epitope.

The DNA reporter construct and a cell which can be transfected with the DNA or a cell which is already transfected with the DNA construct can be provided as reagent kit for investigating RNA export processes. The reagent kit preferably also comprises leptomycin B, because it is possible with this substance specifically to block the RNA export pathway utilized for example by HIV Rev-dependent RNA constructs (Otero, 1998).

The present invention further relates to a method for detecting a viral infection which has taken place, more preferably a retroviral viral infection, most preferably a lentiviral viral infection. The detection is based on the fact that a viral export factor necessary for nuclear export is present in infected cells but not in uninfected cells. If HIV infection is involved, the viral RNA export factor is HIV Rev, and in the case of HTLV infection the viral RNA export factor is HTLV Rex.

Because patients' plasma is easily available, it is appropriate to detect the infection through detecting infectious viruses in the plasma. In this embodiment, a cell which is transfected with the reporter construct, preferably carries the reporter construct stably in itself, particularly preferably has the reporter construct stably integrated into the chromosome, is brought into contact with the patient's plasma. The cell is infected if viruses are present in the plasma. The necessary, trans-active RNA export factor is provided in this way, and RNA export can be detected.

Detection of infection is also possible even if viruses are no longer detectable in the plasma but, nevertheless, cells are infected with the virus. In this case the infection must originate from these cells. An alternative possibility is for the cells also be transfected with the reporter construct.

The infection can, if the reporter gene is chosen suitably, be detected by fluorescent bioanalysis, where appropriate through the autofluorescence of the reporter gene product, preferably by spectroscopy, preferably by fluorescence microscopy, more preferably by FACS analyses. This detection can take place manually or completely automatically in a high-throughput testing.

An infection can be detected through detection of the reporter gene dependent on the viral export factor, in particular Rev, additionally via the enzymatic activity of the chosen reporter gene product, such as the phosphatase activity of SEAP, the acetyltransferase activity of the CAT gene product, the luciferase activity of the luciferase gene. This detection can take place manually or completely automatically in a high-throughput testing.

However, the antigenic properties of a reporter protein or of one or more epitopes of the chosen reporter protein can also be utilized. Detection then takes place by suitable immunological methods such as ELISA, immunofluorescence, immunoblot, FACS of immunologically labeled cells. It is possible manually or completely automatically in a high-throughput testing.

It was possible to show in particular that cells transfected with the Rev-sensitive hivGFP together with an infectious proviral HIV-1 clone (HX10) likewise exhibit a green fluorescent reporter gene activity. The produced Rev-sensitive reporter system is thus suitable for detecting HIV-1 gene expression and thus as detection of infection.

A further detection of the RNA export detection of Lu et al. is the necessity to have to lyse or fix the cells to detect the reporter protein or the activity of the reporter protein. The invention therefore further relates to a method for detecting RNA export from the cell nucleus, in which a reporter protein that can be detected without lysis or fixation of the cells is used. A fluorescent protein for example is suitable for this purpose. However, it is likewise also possible to use a suitable selection marker. The advantage of this method compared with the prior art is the possibility
(a) of being able to transfect or infect the cells with a gene library
(b) of being able to purify the genes which bring about modulation of the RNA export from the cell nucleus by cultivating the cells and isolating the nucleic acid.

EXAMPLES

1. Production of a Rev-Dependent GFP Gene

The intention was to construct artificially the reading frame of the green fluorescent protein (Gfp) gene using a choice of codons like that to be found in HIV-1 structural genes. For this purpose, the amino acid sequence of the Gfp gene was translated into a corresponding nucleotide sequence. This was carried out with the aid of the gcg command "backtranslate" using an appropriate matrix as described in table 1. Further cleavage sites were inserted for subcloning and for attaching further sequence elements within untranslated regions. An exact sequence, including the cleavage sites used, is indicated in SEQ ID No. 9. The sequence produced in this way was produced as completely synthetic gene using synthetic oligonucleotides and a previously described method {Zolotukhin, Potter, 1996}. FIG. 1 depicts a comparison of the hivGFP (choice of codons derived from HIV structural genes) and huGEP (choice of codons derived from mammalian genes). The GFP-encoding DNA fragment ("hivGFP") produced in this way was placed under the transcriptional control of the cytomegalovirus (CMV) early promoter/enhancer ("pc-hivGFP") in the expression vector pcDNA3.1(+) (Stratagen, Heidelberg) using the KpnI and XhoI cleavage sites. To produce an analogous GFP expression plasmid whose choice of codons was, however, adapted to the human system, the coding region of the humanized GFP gene (huGFP) was amplified from a commercially obtainable vector by means of a polymerase chain reaction (PCR) using the oligonucleotides hu-1 and hu-2 and cloned into the expression vector pcDNA3.1(+) (Stratagen, Heidelberg) likewise using the KpnI and XhoI cleavage sites ("pc-huGFP").

As explained in the description, an isolated (efficiently utilizable) splice donor (SD) must be put in front of the coding region in order to achieve Rev dependence of the hivGFP reporter. The HIV-1 untranslated region (UTR) within the late HIV-1 transcripts contains such an SD. This region was amplified by means of PCR using the oligonucleotides utr-1 and utr-2 from proviral HIV-1 DNA (HX10, see (Ratner et al., 1987)) and cloned directly 5' in front of the ATG of the GFP-encoding reading frame of the pc-huGFP and pc-hivGFP constructs using the KpnI and NcoI cleavage sites. The resulting constructs have been referred to hereinafter as "pc-UTR-huGFP" and "pc-UTR-hivGFP", respectively.

As explained in the applications, it is necessary to attach to the coding region an RNA target sequence in order to achieve Rev dependence of the hivGFP reporter. This target sequence interacts at the RNA level either with a viral nuclear export protein (in the case of HIV-1 the Rev protein) or cellular nuclear export proteins. For this reason, the HIV-1 Rev-responsive element from proviral HX10 DNA was amplified by means of PCR using the oligonucleotides rre-1 and rre-2 and cloned 3' behind the GFP-encoding region of the pc-huGFP, pc-UTR-huGFP, pc-hivGFP, pc-UTR-hivGFP constructs using the BamHI and XhoI cleavage sites. The resulting constructs have been referred to hereinafter as "pc-huGFP-RRE", "pc-UTR-huGFP-RRE", "pc-hivGFP-RRE", "pc-UTR-hivGFP-RRE". In addition, the MPMV constitutive transport element CTE from proviral MPMV DNA was amplified by means of PCR using the oligonucleotides cte-1 and cte-2 and cloned 3' behind the GFP-encoding region of the pc-hivGFP, pc-UTR-hivGFP constructs using the BamHI and XhoI cleavage sites. The resulting constructs have been referred to hereinafter as "pc-hivGFP-CTE", "pc-UTR-hivGFP-CTE". All the GFP-encoding constructs produced are depicted diagrammatically in FIG. 2.

For the Norhern blot analyses, additionally the RRE-encoding region was cloned in antisense orientation to the T7 promoter into the pCR-Script vector (Stratagene, Heidelberg). In addition, the pSP6-actin construct was kindly made available to us by F. Schwarzmann's group (IMMH, Regensburg). To provide the viral Rev protein in trans, Prof. J. Hauber (Erlangen) kindly made available a Rev expression plasmid to us.

2. Rev-Dependent GFP Expression of the hivGFP Reporter Requires the Choice of Codons of HIV Structural Genes and the 5'-UTR/SD All the cell culture products were from Life Technologies (Karlsruhe). All mammalian cell lines were cultivated at 37° C. and 5% $CO_2$. The human lung carcinoma cell line H1299 was grown in Dulbecco's modified Eagle medium (DMEM) with L-glutamine, D-glucose (4.5 mg/ml), sodium pyruvate, 10% inactivated fetal bovine serum, penicillin (100 U/ml) and streptomycin (100 µg/ml). The cells were subcultivated in the ratio 1:10 after confluence was reached.

$1.5*10^6$ cells were seeded in Petri dishes (diameter: 100 mm) and, 24 h later, transfected by calcium phosphate coprecipitation (Graham and Eb, 1973) with 30 µg of indicator plasmid and 15 µg of pc-Rev or 15 µg of pcDNA 3.1 vector. Cells and culture supernatants were harvested 48 h after transfection. The transfected cells were washed twice with ice-cold PBS (10 mM $Na_2HPO_4$, 1.8 mM $KH_2PO_4$, 137 mM NaCl, 2.7 mM KCl), scraped off in ice-cold PBS, centrifuged at 300 g for 10 min and lysed in lysis buffer (50 mM Tris-HCl, pH 8.0, 0.5% Triton X-100 (w/v)) on ice for 30 min. Insoluble constituents of the cell lysate were removed by centrifugation at 10 000 g and 4° C. for 30 min. The total amount of protein in the supernatant was determined using the Bio-Rad Protein Assay (Bio-Rad, Munich) in accordance with the manufacturer's instructions.

The samples were mixed with the same volume of 2× sample buffer (Laemmli, 1970) and heated at 95° C. for 5 min. 50 µg of total protein from cell lysates or half the sample batch from enriched supernatants (B.4.1) were fractionated on a 12.5% SDS/polyacrylamide gel (Laemmli, 1970) electrotransferred to a nitrocellulose membrane and analyzed using the monoclonal $p^{24}$-specific antibody 13-5 (Wolf et al., 1990) and detected by means of a secondary, HRP (horseradish preoxidase)-coupled antibody and detected by chromogenic staining.

The reporter constructs were transiently transfected into H1299 cells. The expression achieved was analyzed in the presence and absence of Rev/RRE and of the 5'-UTR/SD. The huGFP expression could not be enhanced either by the Rev/RRE system (FIG. 3A, lanes 3, 4), nor was it significantly influenced by the 5'-UTR/SD (FIG. 3A, lane 5). Nor was the combination of 5'-UTR/SD and Rev/RRE able to convert the synthetic reading frame into Rev dependence (FIG. 3A, lane 6). However, in contrast to this, the hivGFP reporter constructs adapted to the choice of codons of HIV-1 structural genes behaved completely differently. Thus, no GFP expression was detectable in the absence of the 5'-UTR/SD, irrespective of the presence or absence of the Rev/RRE system (FIG. 3A, lane 7, 8). Only in the presence of the 5'-UTR/SD and of the hivGFP reporter gene adapted to HIV-1 structural genes was it possible to detect Rev/RRE-dependent expression of the GFP reporter (FIG. 3A, cf. lane 9 with 10).

Rev-dependent expression based on nuclear export of viral or quasi-viral transcripts should not be attributable by a simple stabilization of the transcripts by the Rev/RRE interaction alone. Although the Rev-M10 mutant can interact with the RNA target sequence RRE and other Rev proteins (mutated as well as wild type), it cannot be exported from the nucleus due to a defect within the nuclear export signal (NES) (Stauber et al, 1995; Kubota et al, 1991). GFP expression could not be achieved in the presence of the Rev-M10 protein after transfection with the UTR-hivGFP-RRE reporter (FIG. 3B, lane 3). Rev-dependent expression of the hivGFP reporter is thus not attributable to stabilization of the RNA by a Rev/RRE interaction but to the subsequent nuclear export through wild-type Rev. It was moreover possible through the UTR-hivGFP-RRE reporter to achieve GFP expression in the presence of cotransfected proviral HIV-1 DNA (HX10) (FIG. 3B, lane 2). It is thus possible to detect an HI viral infection by means of the Rev formed during viral replication by the hivGFP reporter system. In addition, hivGFP expression using the heterologous CTE nuclear translocation system likewise proved to be dependent on the presence of the 5'-UTR/SD and on the choice of codons used (FIG. 3C). This shows that the reporter system based on this invention is based on a superordinate nuclear retention principle which operates irrespective of the nuclear export mechanism.

3. Rev-Dependent GFP Expression of the hivGFP Reporter is Based on Rev-Mediated Nuclear Translocation The experiments summarized in FIG. 3 suggest that there is Rev-mediated nuclear export of the UTR-hivGFP-RRE transcripts. In order to prove this suggestion, the subcellular distribution of the GFP-encoding transcripts was subjected to Northern blot analysis. GFP-encoding transcripts were detected using an RRE-specific probe. In addition, the amount and integrity of the β-actin RNA were detected as internal control of the quality and quantity of the RNA preparation.

For this purpose, transfected cells were detached by trypsinization and washed 2× with ice-cold PBS. 1×10$^7$ cells were partially lysed with 175 µl of lysis buffer (50 mM Tris, 140 mM NaCl, 1.5 mM MgCl$_2$, 0.5% NP-40, pH 8.0) on ice for 5 min. The cytoplasmic fraction was separated from the nuclear fraction by centrifugation (300×g, 2 min) and placed on ice. The nuclei were cautiously washed with lysis buffer and again centrifuged (300×g, 2 min). The total DNA was prepared from the nuclei and from the cytoplasmic fraction in each case using the RNeasy kit (Qiagen, Hilden). The RNA preparations were taken up in RNAase-free water and stored at −80° C. until used further.

The following solutions were used for the Northern blot analysis:

| | |
|---|---|
| SSPE (20x): | 175.3 g of NaCl, 27.6 g of NaH$_2$PO$_4$ H$_2$O, 7.4 g of EDTA add 1 1 1 1 of H$_2$O (adjust to pH 7.4) |
| MOPS (10x): | 83.72 g of MOPS, 8.23 g of NaAc, 20 ml of EDTA (0.5 M) add 1 1 of H2O (adjust to pH 7.0) |
| SSC (20x): | 87.7 g of NaCl, 44.1 g of Na citrate add 500 ml of H2O (adjust to pH 7.0) |
| Denhards (100x): | 1 g of Ficoll (type 400), 1 g of polyvinylpyrrolidones, 1 g of BSA (fraction V) add 50 ml of H2O |
| Hybridization buffer: | 12.5 ml of SSPE (20x), 25 ml of formamide, 2.5 of Denhards (100x), 2.5 ml of SDS (10%), 20 mg of tRNA (from brewers yeast, Boeringer Mannheim) |
| RNA sample buffer: | 10.0 ml of formamide, 3.5 ml of foraldehyde, 2.0 ml of MOPS (5x) |
| RNA loading buffer: | 50% of gylcerol, 1 mM of EDTA, 04% bromophenol blue |

The Northern blot analyses were carried out on the basis of the "Promega" protocol (RNA Applications Guide, Promega Corporation, Madison, USA). 10 µl of RNA preparation were provided with 20 µl of sample buffer and 5 µl of loading buffer and fractionated on a 1% agarose gel (0.04M MOPS, 0.01M NaAc, 0.001M EDTA, 6.5% formaldehyde, pH 7.0). The RNA, gel was blotted by capillary force on a negatively charged nylon membrane (Boehringer, Mannheim) overnight. The RNA was fixed on the membrane by UV treatment (1200 kJ for 1 min), and nucleic acids were stained nonspecifically (0.03% methylene blue, 0.3M NaAc). The size standard, and the 18S and 28S RNA were marked and the blot was decolorized in water. The membrane was preincubated in 10 ml of hybridization buffer at 60° C. for 2 h and hybridized overnight after addition of a radiolabeled RNA probe. The blot was then evaluated after stringent washing several times (0.1 SSC, 01% SDS) by exposure on a Phosphor-Imager plate and with the aid of the Molecular Analyst software (Bio-Rad Laboratories, Munich).

Radioactive antisense RNA probes for specific detection of the RNA were produced by in vitro transcription using the Riboprobe in vitro transcription system (Promega, Madison, USA), observing the manufacturer's instructions. The radiolabeled nucleotide used was $^{32}$P-α-CTP (10 µCi per reaction). The transcription template employed in each case was 500 ng of linearized plasmid DNA. An RRE-specific RNA probe was produced by T7-mediated transcription of XhoI-linearized pc-ERR. A β-actin-specific RNA probe was produced by SP6-mediated transcription of EcoRI-linearized pSP6-actin.

The amounts of cytoplasmic RNA correlated for all the reporter constructs with the measured GFP expression (FIG. 4, lanes 7-12). In the absence of the 5'-UTR it was possible to detect only minimal amounts of hivGFP RNA (hivGFP-RRE) in the nucleus, even when Rev was made available in trans (FIG. 4, lane 5, 6). In contrast to this, in the presence of the authentic 5'-UTR (UTR-hivGFP-RRE), the GFP RNAs adapted to the choice of codons of HIV structural genes accumulated in the nucleus and were detectable in large amounts therein (FIG. 4, lane 1).

Without adaptation of the choice of codons to HIV-1 structural genes, the huGFP RNA proved to be stable in the nucleus and was constitutively transported into the cytoplasm, even when the 5'-UTR/SD was placed in front of the coding region. It is thus impossible solely by placing an efficiently utilized SD in front to convert any particular gene into Rev dependence in the absence of an (efficiently utilized) SA.

Rev-dependent GFP expression of hivGFP can be inhibited with therapeutic agents which block Rev-mediated nuclear export. As described in the applications, it was possible to use the Rev-dependent hivGFP reporter system described herein for identifying therapeutic agents with antiviral activity, especially those which inhibit the nuclear export of the quasi-viral GFP-encoding RNA. Leptomycin B (LMB) and the trans-dominant-negative Rev mutant M10 (Rev M10) are the best known inhibitors of Rev-mediated nuclear export. These established active substances should likewise have an inhibitory effect on Rev-dependent expression of the hivGFP reporter. In order to test this, hivGFP expression was analyzed in the presence of Rev and LMB or Rev M10.

For the Rev M10 experiments, $3 \times 10^5$ H1299 cells were seeded in a 6-well cell culture plate and, 24 h later, transfected with 5 µg of reporter plasmid, 2.5 µg of pc-Rev and increasing amounts of pc-RevM10 by calcium phosphate coprecipitation. In addition, the transfection mixture was adjusted in each case to a total of 15 µg of total DNA with pcDNA 3.1 plasmid DNA.

For the LMB experiments, $3 \times 10^5$ H1299 cells were seeded in a 6-well cell culture plate and, 24 h later, transfected with 10 µg of reporter plasmid and 5 µg of pc-Rev or pcDNA 3.1 plasmid DNA by calcium phosphate coprecipitation. 24 h before harvesting, the medium was supplemented with 5 nM of LMB. The cells were harvested and GFP expression was read as described above.

It was possible even by cotransfection with equimolar amounts of RevM10 to reduce greatly Rev-dependent expression of the UTR-hivGFP-RRE reporter construct (FIG. 5A). It was likewise possible to inhibit only the expression of the Rev-dependent GFP reporter through the presence of 5 nM LMB, but not the expression of the huGFP reporter (FIG. 5B). It was thus possible to demonstrate that the hivGFP RNA leaves the cell nucleus by the same nuclear export pathway (CRM1) as late HIV-1 transcripts. It was additionally possible to demonstrate that GFP expression of the established Rev-dependent GFP reporter can be inhibited by Rev inhibitors in the same way as the expression of late HIV-1 genes. The simple autofluorescent detection of the GFP reporter thus makes this suitable for identifying Rev inhibitors with antiviral activity. Rev-dependent GFP expression of the hivGFP reporter can be detected on a single-cell basis and can be quantified by flow cytometry.

The autofluorescent properties of GFP permit detection of Rev-dependent expression of the hivGFP reporter system on a single-cell basis. For microscopic decetion, sterile slides were for this purpose placed in Petri dishes, $10^6$ H1299 cells seeded thereon and, 24 h later, transfected with 30 µg of GFP reporter plasmid and 15 µg of pc-Rev or 15 µg of pcDNA 3.1(+) by calcium phosphate coprecipitation. After 48 h, the slides were washed 2× with PBS, fixed with 4% paraformaldehyde (10 min) and then stained with DAPI (1 mg/ml) at 37° C. for 1 h. Microscopic detection of the GFP gene product took place with the aid of an Olympus AX500 fluorescent microscope.

In the case of the reporter based on huGFP there was detectable GFP activity unaffected by the presence and absence of Rev. By contrast, green fluorescent reporter activity of the GFP was detectable in UTR-hivGFP-RRE-transfected cells only when Rev was cotransfected (FIG. 6). Detection of the Rev-dependent GFP reporter is thus possible on a single-cell basis.

In order to be able to quantify this better, in addition the GFP activity of transfected cells was subjected to an FACS analysis. For the analysis in a flow cytometer, $10^6$ H1299 cells were seeded in Petri dishes and, 24 h later, transfected with 30 µg of reporter construct and 15 µg of pc-Rev or pcDNA 3.1(+) by calcium phosphate coprecipitation. The transfected cells were detached by trypsinization 48 h later, taken up in ice-cold PBS and subjected to an FACS analysis. The results have been represented in a 2-dimensional diagram. For this purpose, the fluorescence intensity (x axis) was plotted against the cell count (y axis). It was possible to confirm the results of the expression analyses using the Western blot technique by the FACS analyses. Once again, the Rev/RRE system brought about no increase in GFP expression, irrespective of the presence or absence of the 5'-UTR (FIG. 7, 2 to 4). Only in the GFP reporter constructs whose choice of codons was adapted to that of HIV-1 structural genes and simultaneously had a 5'-UTR/SD was it possible to detect Rev/RRE-dependent GFP reporter activity. In the presence of Rev and RRE it was possible to increase the GFP activity of the hivGFP reporter from a scarcely detectable background activity (2.2% of huGFP) to more than 15 times the level (36.2% of huGFP). The GFP reporter construct produced on the basis of this invention accordingly permits quantitative detection of Rev-mediated nuclear export on a single basis and is thus suitable for high-throughput testing.

```
utr-1:
                                             (SEQ ID NO: 1)
gat cga att ccg acg cag gac tcg gct tgc utr-2:
                                             (SEQ ID NO: 2)
gat ccc atg gct ctc tcc ttc tag cct ccg rre-1:
                                             (SEQ ID NO: 3)
gat cgg atc cga gat ctt cag acc tgg agg ag rre-2:
                                             (SEQ ID NO: 4)
gat cct cga ggt tca cta atc gaa tgg atc tg hu-1:
                                             (SEQ ID NO: 5)
gat cga att caa cca tgg tga gca agg gcg agg ag hu-2:
                                             (SEQ ID NO: 6)
gat cct cga gaa gga tcc ttt act tgt aca gct cgt c cte-1:
                                             (SEQ ID NO: 7)
gct agg atc ccc att atc atc gcc tgg aac cte-2:
                                             (SEQ ID NO: 8)
cga act cga gca aac aga ggc caa gac atc
```

TABLE 1

Preferred choice of codons for producing a Rev-dependent gene.

| Amino acid | Codon | Priority |
|---|---|---|
| Ala | GCA | 1 |
| Ala | GCT | 2 |
| Arg | AGG | 2 |

TABLE 1-continued

Preferred choice of codons for producing a Rev-dependent gene.

| Amino acid | Codon | Priority |
|---|---|---|
| Arg | AGA | 1 |
| Asn | AAT | 1 |
| Asn | AAC | 2 |
| Asp | GAT | 2 |
| Asp | GAC | 1 |
| Cys | TGT | 1 |
| Cys | TGC | 2 |
| End | TAG | 2 |
| End | TAA | 1 |
| Gln | CAG | 2 |
| Gln | CAA | 1 |
| Glu | GAG | 2 |
| Glu | GAA | 1 |
| Gly | GGG | 2 |
| Gly | GGA | 1 |
| His | CAT | 1 |
| His | CAC | 2 |
| Ile | ATA | 1 |
| Ile | ATT | 2 |
| Leu | TTA | 1 |
| Leu | CTA | 2 |
| Lys | AAG | 2 |
| Lys | AAA | 1 |
| Met | ATG | 1 |
| Phe | TTT | 1 |
| Phe | TTC | 2 |
| Pro | CCA | 1 |
| Pro | CCT | 2 |
| Ser | AGC | 1 |
| Ser | TCA | 2 |
| Thr | ACA | 1 |
| Thr | ACT | 2 |
| Trp | TGG | 1 |
| Tyr | TAT | 1 |
| Tyr | TAC | 2 |
| Val | GTA | 1 |
| Val | GTG | 2 |

Priority 1: preferred codon
Priority 2: preferred codon if codon of priority 1 is not used.

REFERENCES

Ausubel, F. M., Brent, R., Kingston, R. E., Moore, D. D., Seidman, J. G., Smith, J. A., and Struhl, K. (1994). Percentage of Codon Synonomous Usage and Frequency of Codon Occurrence in Various Organisms. Current Protocols in Molecular Biology 2, A1.8-A1.9

Borg, K. T., Favaro, J. P., and Arrigo, S. J. (1997). Involvement of human immunodeficiency virus type-1 splice sites in the cytoplasmic accumulation of viral RNA. Virology 236, 95-103.

Chang, D. D. and Sharp, P. A. (1989). Regulation by HIV Rev depends upon recognition of splice sites. Cell 59, 789-795.

Chen, C. Y. and Shyu, A. B. (1995). AU-rich elements: characterization and importance in mRNA degradation. Trends. Biochem. Sci. 20, 465-470.

Cochrane, A. W., Jones, K. S., Beidas, S., Dillon, P. J., Skalka, A. M., and Rosen, C. A. (1991). Identification and characterization of intragenic sequences which repress human immunodeficiency virus structural gene expression. J. Virol. 65, 5305-5313.

Graham, F. L. and Eb, A. J. (1973). A new technique for the assay of infectivity of human adenovirus 5 DNA. Virology 52, 456-467.

Kaufmann, R. (1979). High level production of proteins in mammalian cells. Genetic engineering, eds. Setlow, J. K. and Hollaender, A., New York, Plenum Press, 155-198.

Kjems, J., Frankel, A. D., and Sharp, P. A. (1991). Specific regulation of mRNA splicing in vitro by a peptide from HIV-1 Rev. Cell 67, 169-178.

Kjems J. and Sharp, P. A. (1993). The basic domain of Rev from human immunodeficiency virus type 1 specifically blocks the entry of U4/U6.U5 small nuclear ribonucleoprotein in spliceosome assembly. J. Virol. 67, 4769-4776.

Kubota, S., Nosaka, T., Furuta, R., Maki, M., Hatanaka, M. (1991). Functional conversion from HIV-1 Rev to HTLV-1 Rex by mutation. Biochem. Biophys. Research Commun. 178:1226-1232.

Laemmli, U. K. (1970). Cleavage of structural proteins during the assembly of the head of bacteriophage T4. Nature 227, 680-685.

Lu, X. B., Heimer, J., Rekosh, D., and Hammarskjold, M. L. (1990). U1 small nuclear RNA plays a direct role in the formation of a rev-regulated human immunodeficiency virus env mRNA that remains unspliced. Proc. Natl. Acad. Sci. U.S.A. 87, 7598-7602.

Luo, Y., Yu, H., and Peterlin, B. M. (1994). Cellular protein modulates effects of human immunodeficiency virus type 1 Rev. J. Virol. 68, 3850-3856.

Maldarelli, F., Martin, M. A., and Strebel, K. (1991). Identification of posttranscriptionally active inhibitory sequences in human immunodeficiency virus type 1 RNA: novel level of gene regulation. J. Virol. 65, 5732-5743.

Malim, M. H. and Cullen, B. R. (1993). Rev and the fate of pre-mRNA in the nucleus: implications for the regulation of RNA processing in eukaryotes. Mol. Cell. Biol. 13, 6180-6189.

Mikaelian, I., Krieg, M., Gait, M. J., and Karn, J. (1996). Interactions of INS (CRS) elements and the splicing machinery regulate the production of Rev-responsive mRNAS. J. Mol. Biol. 257, 246-264.

Nasioulas, G., Zolotukhin, A. S., Tabernero, C., Solomin, L., Cunningham, C. P., Pavlakis, G. N., and Felber, B. K. (1994). Elements distinct from human immunodeficiency virus type 1 splice sites are responsible for the Rev dependence of env mRNA. J. Virol. 68, 2986-2993.

O'Reilly, M. M., McNally, M. T., and Beemon, K. L. (1995). Two strong 5' splice sites and competing, suboptimal 3' splice sites involved in alternative splicing of human immunodeficiency virus type 1 RNA. Virology 213, 373-385.

Olsen, H. S., Cochrane, A. W., and Rosen, C. (1992). Interaction of cellular factors with intragenic cis-acting repressive sequences within the HIV genome. Virology 191, 709-715.

Otero, G. C., Harris, M. E., Donello, J. E. and Hope, T. J. (1998). Leptomycin B inhibits equine infections anemia virus Rev and feline immunodeficiency virus Rev function, but not the function of the hepatitis B virus posttranscriptional regulatory element. J. Virol. 72, 7593-7597.

Pollard, V. W. and Malim, M. H. (1998). The HIV-1 Rev protein [In Process Citation]. Annu. Rev. Microbiol. 52:491-532, 491-532.

Powell, D. M., Amaral, M. C., Wu, J. Y., Maniatis, T., and Greene, W. C. (1997). HIV Rev-dependent binding of SF2/ASF to the Rev response element: possible role in Rev-mediated inhibition of HIV RNA splicing. Proc. Natl. Acad. Sci. U.S.A., 94, 973-978.

Ratner, L., Fisher, A., Jagodzinski, L. L., Mitsuya, H., Liou, R. S., Gallo, R. C., and Wong Staal, F. (1987). Complete nucleotide sequences of functional clones of the AIDS virus. AIDS Res. Hum. Retroviruses 3, 57-69.

Rosen, C. A., Terwilliger, E., Dayton, A., Sodroski, J. G., and Haseltine, W. A. (1988). Intragenic cis-acting art gene-responsive sequences of the human immunodeficiency virus. Proc. Natl. Acad. Sci. U.S.A., 85, 2071-2075.

Schneider, R., Campbell, M., Nasioulas, G., Felber, B. K., and Pavlakis, G. N. (1997). Inactivation of the human immunodeficiency virus type 1 inhibitory elements allows Rev-independent expression of Gag and Gag/protease and particle formation. J. Virol. 71, 4892-4903.

Schwartz, S., Campbell, M., Nasioulas, G., Harrison, J., Felber, B. K., and Pavlakis, G. N. (1992a). Mutational inactivation of an inhibitory sequence in human immunodeficiency virus type 1 results in Rev-independent gag expression. J. Virol. 66, 7176-7182.

Schwartz, S., Felber, B. K., and Pavlakis, G. N. (1992b). Distinct RNA sequences in the gag region of human immunodeficiency virus type 1 decrease RNA stability and inhibit expression in the absence of Rev protein. J. Virol. 66, 150-159.

Stauber, R., Gaitanaris, G. A., and Pavlakis, G. N. (1995). Analysis of trafficking of Rev and transdominant Rev-proteins in living cells using green fluorescent protein fusions: transdominant Rev blocks the export of Rev from the nucleus to the cytoplasm. Virology 213, 439-449.

BRIEF DESCRIPTION OF DRAWINGS

FIG. 1: A sequence comparison of the humanized GFP gene versus the hivGFP gene whose choice of codons has been adapted to that of HIV-1 structural genes is depicted. Almost every third wobble position has been replaced mostly by an A or T. This reduces the homology of the two reading frames to 67.9%. The total AT content thus increases from about 37% (huGFP) to about 69% (hivGFP), but without changing the amino acid sequence of the resulting gene products (SEQ ID NOS 9 & 10 are disclosed respectively in order of appearance).

FIG. 6: Immunofluorescence analysis of the huGFP and hivGFP reporter. H1299 cells were transfected with the stated constructs and cotransfected with Rev or blank vector (no Rev) on slides. After 48 h, the cells were fixed and stained with DAPI, and the autofluorescent activity of the GFP gene product was evaluated in an immunofluorescent microscope.

SEQUENCE LISTING

Figure 2:
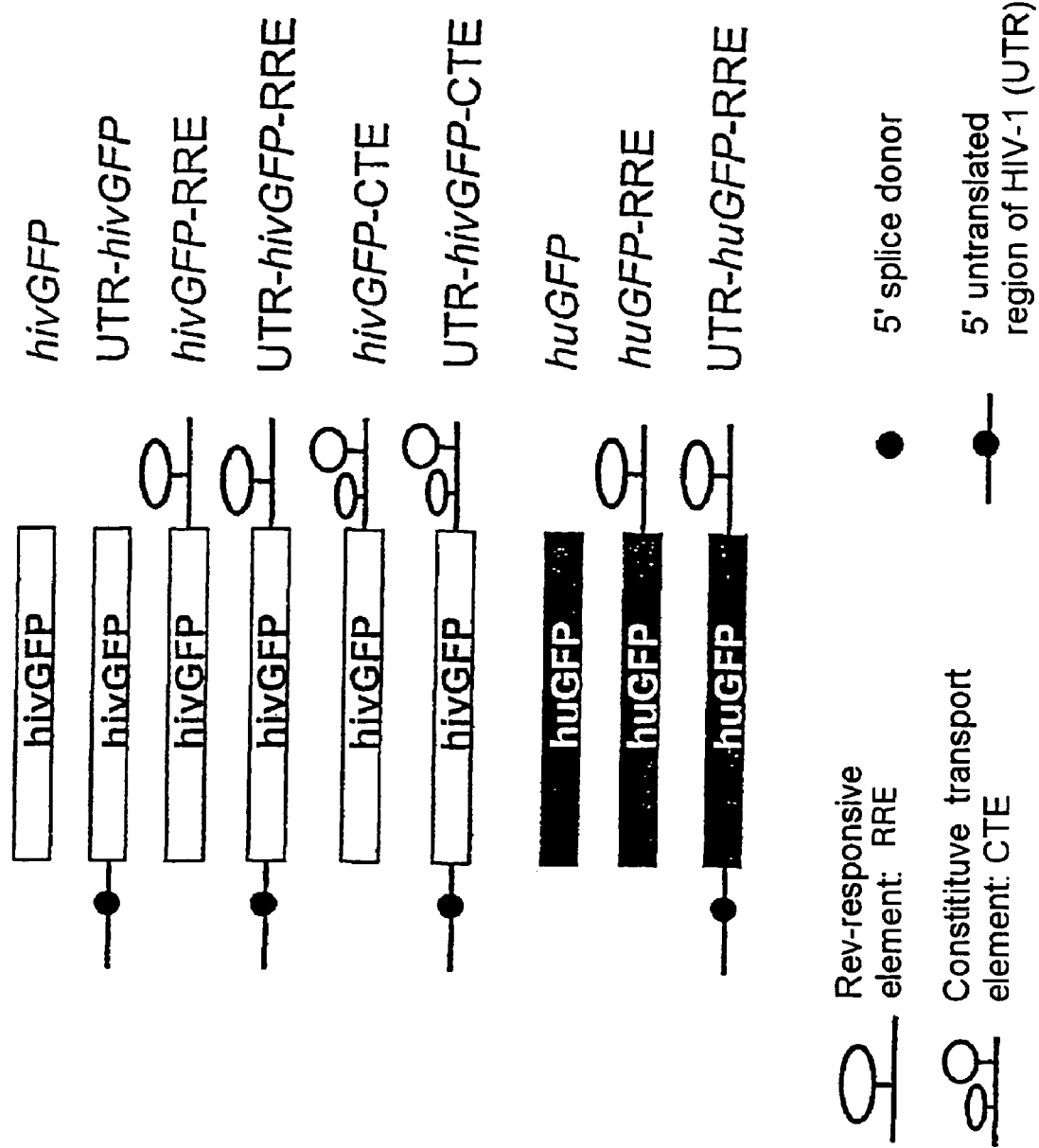
FIG. 2: Diagrammatic representation of all the GFP reporter constructs produced and used in this study. Open boxes symbolize GFP genes (hivGFP) adapted to HIV structural genes, and black boxes symbolize GFP genes (huGFP) adapted to mammalian genes. Horizontal lines symbolize untranslated regions. All other symbols are explained underneath the image.
Figure 3A:
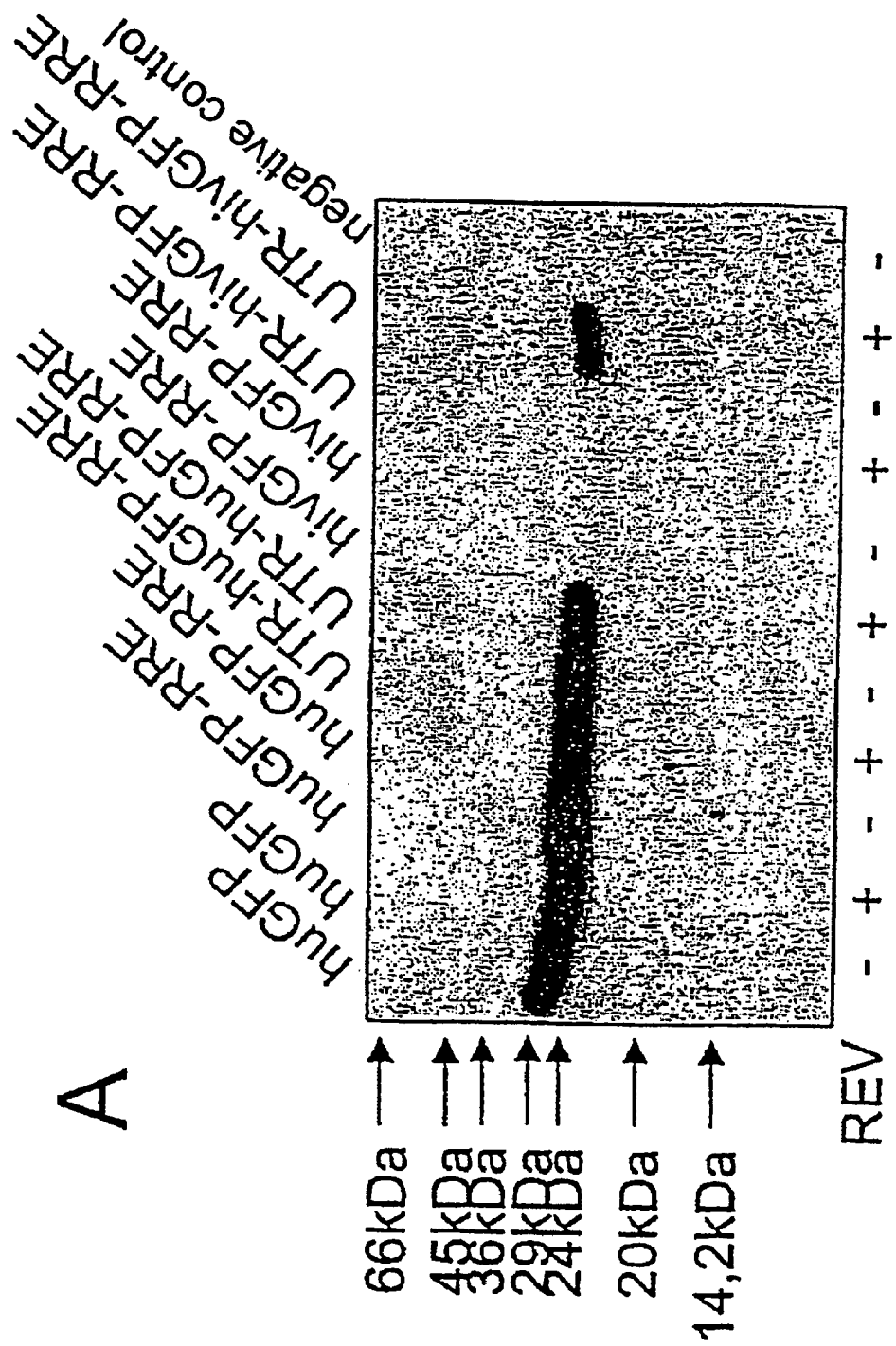
FIG. 3: Expression analysis of the synthetic reading frames. H1299 cells were transfected with the stated GFP constructs, and cotransfected with the vectors (+) indicated below the images or blank vector (−). GFP production was detected by conventional immunoblot analysis. (A) Testing of a Rev-dependent GFP expression. (B) Testing of GFP expression of UTR-hivGFP-RRE in the presence of Rev, of a mutated form of Rev (Rev M10) and of proviral HIV-1 DNA (HX10). (C) Testing of a CTE-mediated GFP expression of the reporter constructs. Position and molecular weight of the GF protein are indicated by an arrow on the right-hand margin.
Figure 3:
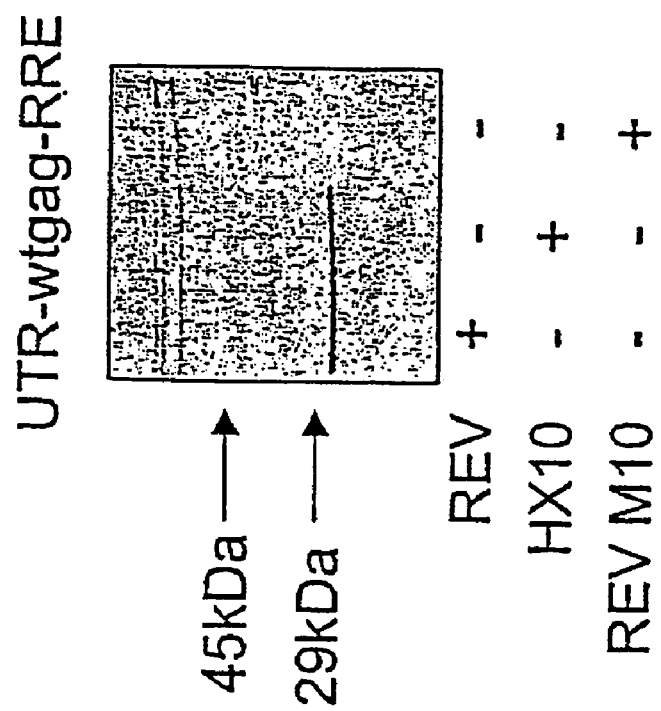
Figure 4:
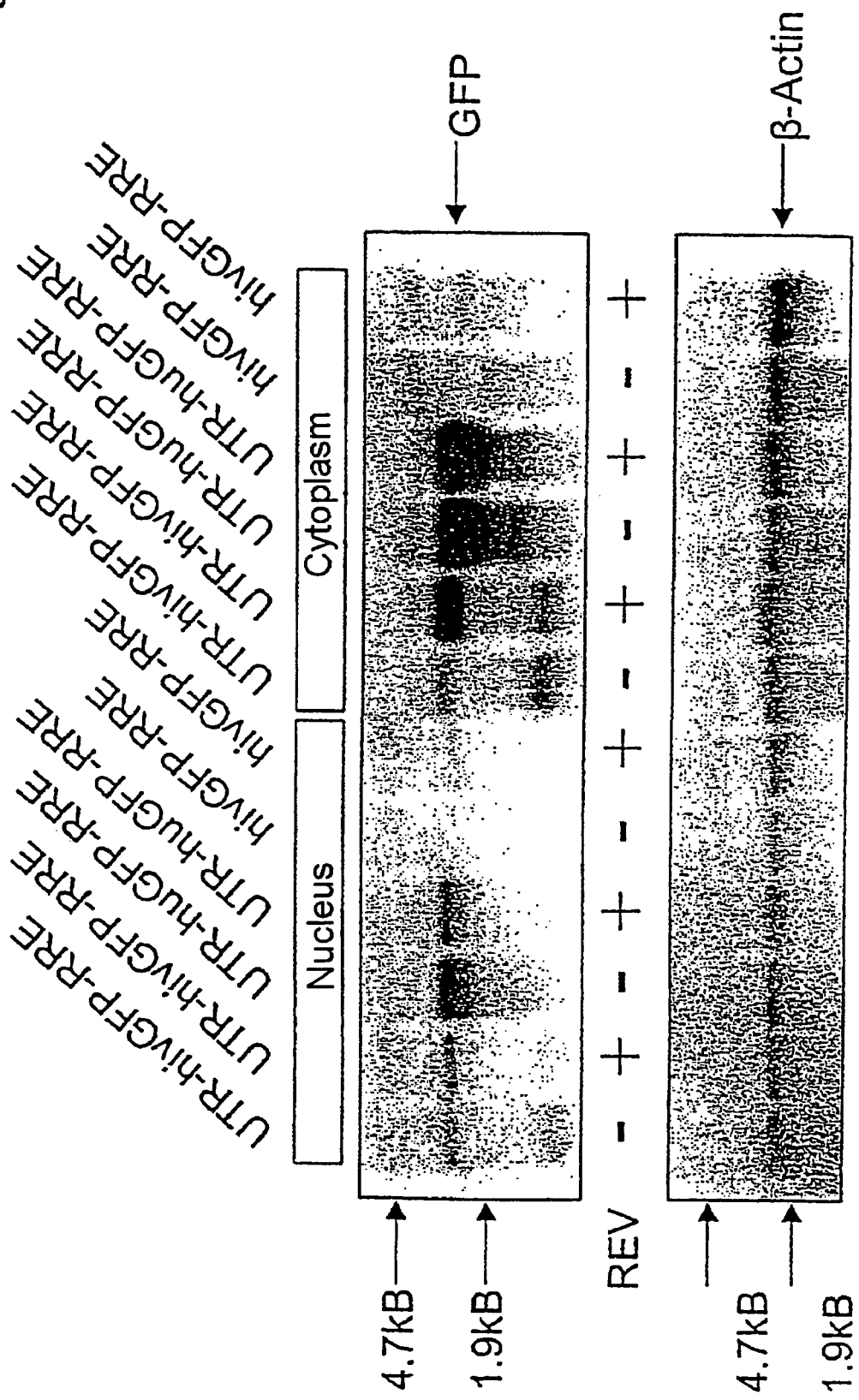
FIG. 4: Northern blot analysis and subcellular distribution of GFP-encoding RNAs. Transfected H1299 cells were partially lysed with 0.5% NP-40 buffer, and the nuclei were separated from the cytoplasm by centrifugation. The total RNA was prepared in each case from the nuclear and cytoplasmic fraction and subjected to a Northern blot analysis. GFP transcripts adapted to HIV-1 structural genes and adapted to mammalian genes were detectable simultaneously by means of an RRE-specific probe. The size and position of the GFP RNA is indicated by an arrow. As internal control, the RNA of the housekeeping gene β-actin was likewise detected.
Figure 5A:
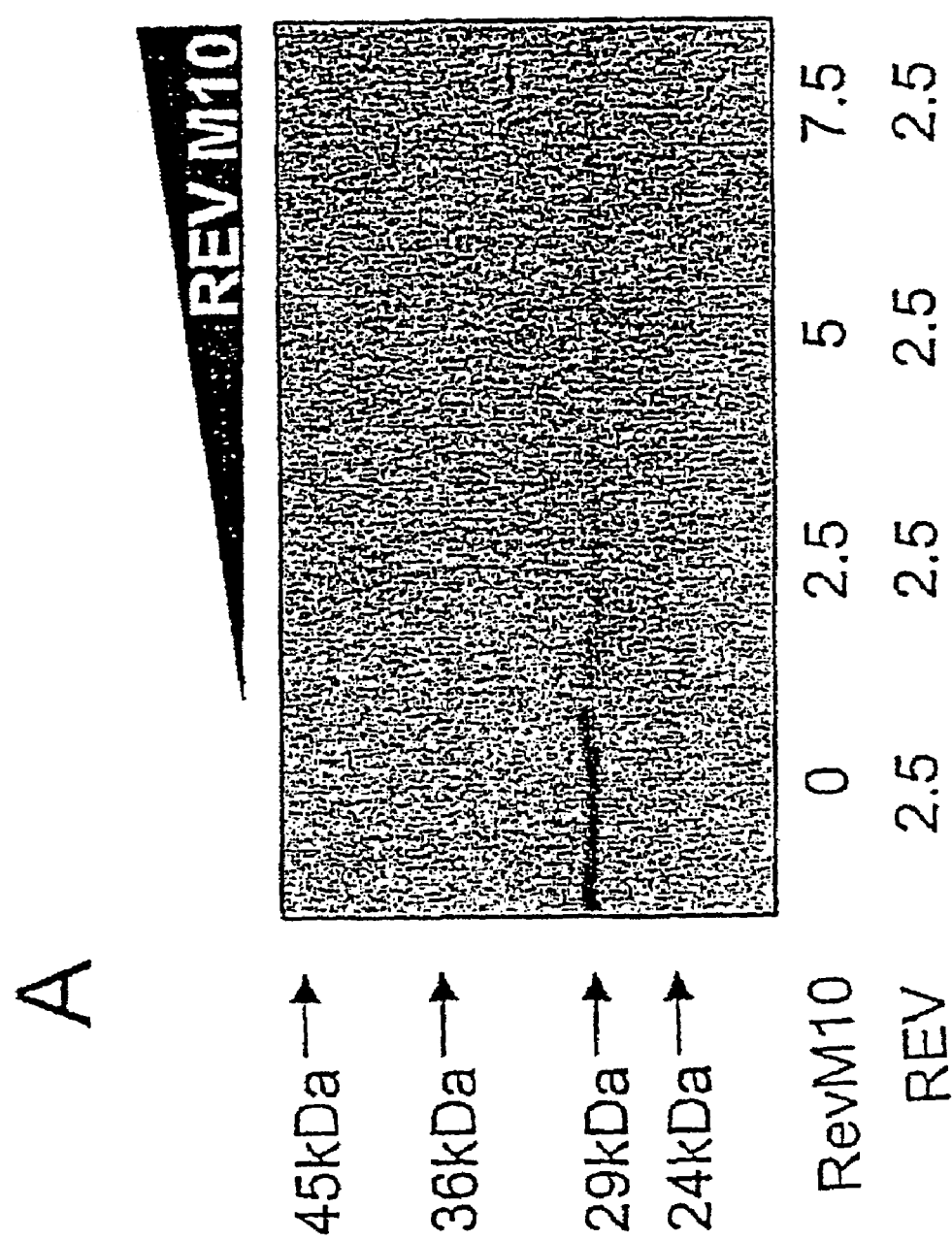
FIG. 5: Effect of Rev inhibitors on the expression of the GFP reporters. H1299 cells were transfected with the stated GFP constructs and analyzed by Western blotting. (A) To test the effect of the transdominant Rev mutant (Rev M10) on GFP expression of the UTR-hivGFP-RRE reporter, 5 μg of the reporter were cotransfected with in each case with 2.5 μg of Rev plasmid and increasing amounts of Rev M10 expression plasmid (0; 2.5; 5; 7.5). (B) To test the effect of LMB on GFP expression, the stated constructs were cotransfected in the presence (+) and absence (−) of 5 nM LMB, and Rev(+) and blank vector (−).
Figure 7:
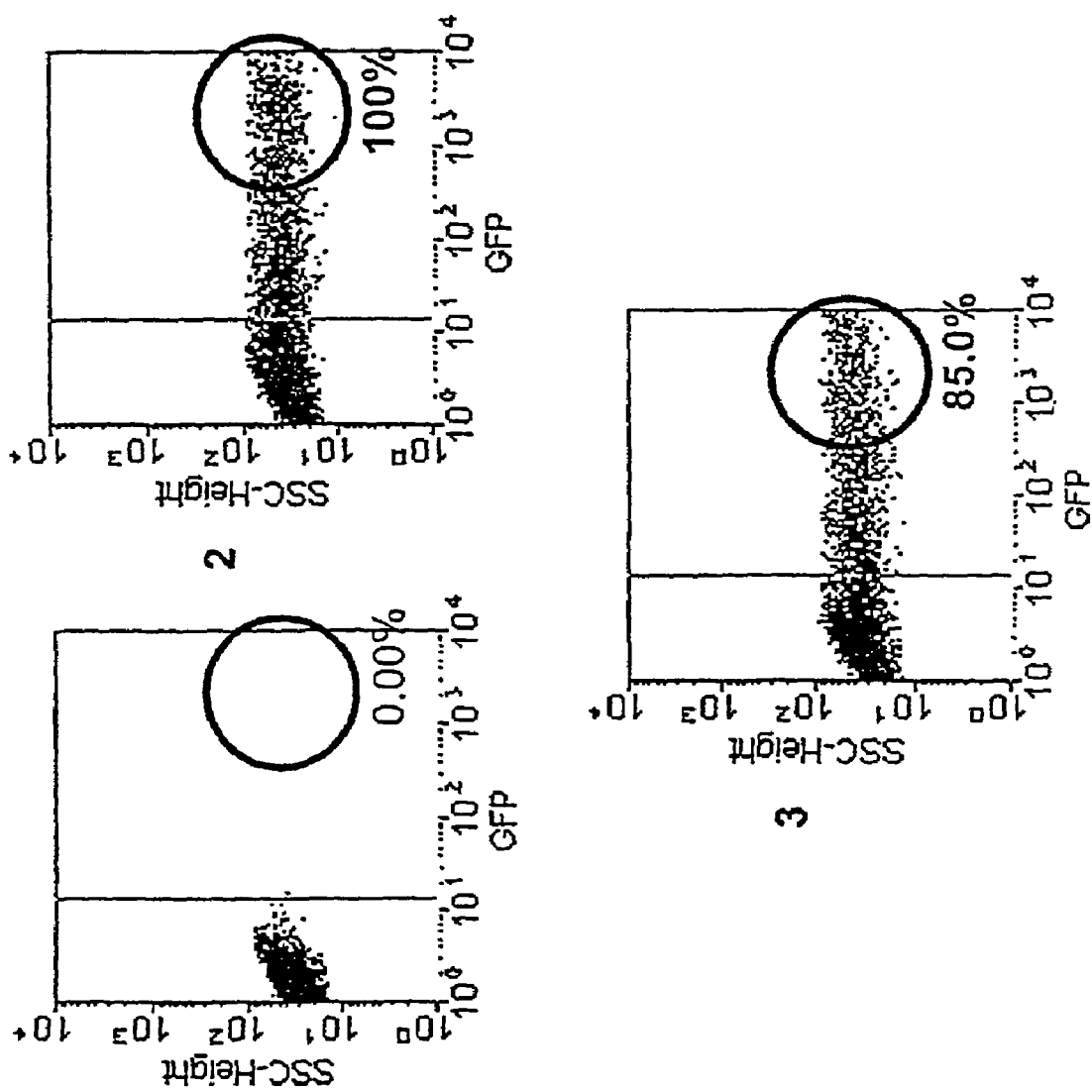
FIG. 7: Flow cytometry analysis of transfected H1299 cells. 1: Mock, 2: huGFP, 3: UTR-huGFP-RRE, 4: UTR-huGFP-RRE and REV., 5: hivGFP-RRE, 6: hivGFP-RRE and REV, 7: UTR-hivGFP-RRE, 8: UTR-hivGFP-RRE and REV. The Y axis indicates the scattered light intensity, and the X axis indicates the GFP-related fluorescence. The vertical line divides the cell populations into (left) non-fluorescent and measurable fluorescent GFP activity (right). The percentage amounts of cells are indicated at the top in the analyses. The red circles include cell population with high fluorescent GFP activity. The percentage amounts of these cells are indicated below in the analyses (marked red).
Figure 7:
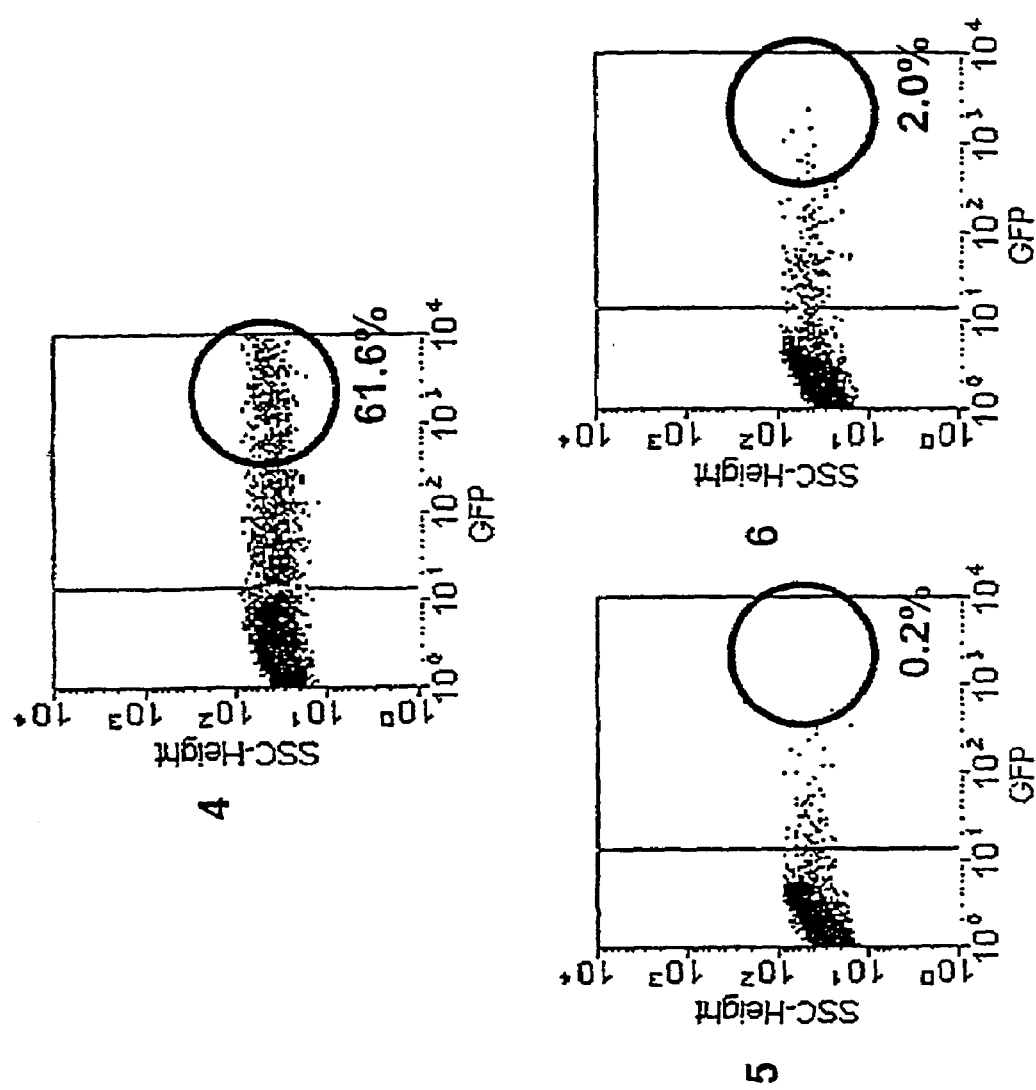
Figure 7:
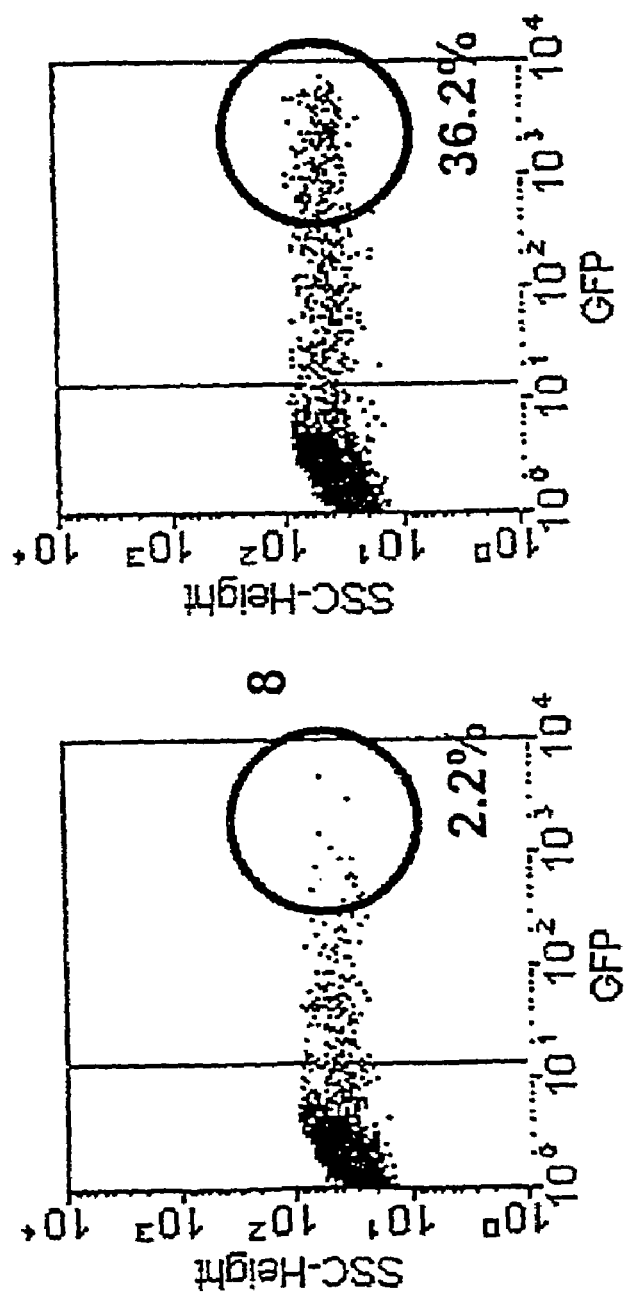
Figure 8:
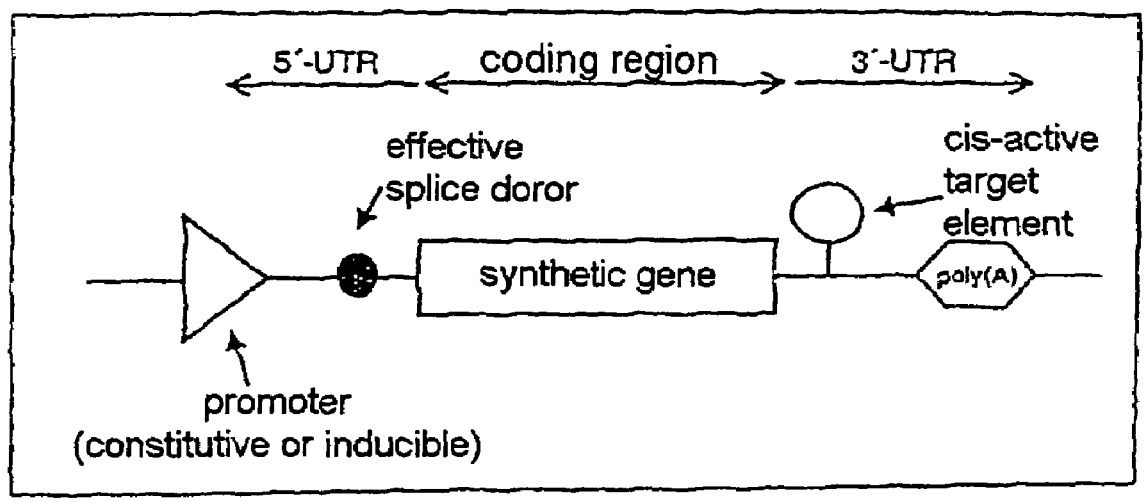
FIG. 8: Diagrammatic representation of a Rev-dependent gene. The synthetic gene must have a choice of codons which is unusual for mammalian genes or a thoroughly high (>50%) A/T content. An untranslated region (UTR) which comprises an effective splice donor is positioned 5' from this gene. The viral target sequence must be positioned 3' from this gene. This target sequence may be either a constitutive transport element such as of the MPMV CTE, or the target sequence of a viral RNA transport molecule such as of the HIV-1 RRE. Cellular or viral export factors then mediate the nuclear export. The Rev-dependent gene is under the transcriptional control of an inducible (Tet on/off) or constitutive (CMV, SV40) promoter. Polyadenylation of the transcripts is ensured by a polyadenylation signal such as of the BGHpoly(A) signal.

```
<160> NUMBER OF SEQ ID NOS: 10

<210> SEQ ID NO 1
<211> LENGTH: 30
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 1
gatcgaattc cgacgcagga ctcggcttgc                                           30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gatcccatgg ctctctcctt ctagcctccg                                           30

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatcggatcc gagatcttca gacctggagg ag                                        32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatcctcgag gttcactaat cgaatggatc tg                                        32

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatcgaattc aaccatggtg agcaagggcg aggag                                     35

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatcctcgag aaggatcctt tacttgtaca gctcgtc                                   37

<210> SEQ ID NO 7
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 7
gctaggatcc ccattatcat cgcctggaac                                           30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cgaactcgag caaacagagg ccaagacatc                                           30

<210> SEQ ID NO 9
<211> LENGTH: 720
<212> TYPE: DNA
<213> ORGANISM: Human immunodeficiency virus

<400> SEQUENCE: 9
atggtaagca aaggagaaga attatttaca ggagtagtac aatatattgt agaattagac          60
ggtgacgtaa atggacataa atttagcgta agcggagaag gagaaggtga cgcaacatat        120
ggaaaattaa cattaaaatt tatatgtaca acaggaaaat taccagtacc ctggccaaca        180
ttagtaacaa catttacata tggagtacaa tgttttagca gatatccaga ccatatgaaa        240
caacatgact tttttaaaag cgcaatgcca gaaggatatg tacaagaaag aacaatattt        300
tttaaagacg acggaaatta taaacaaga gcagaagtaa aatttgaagg agacacatta         360
gtaaatagaa tagaattaaa aggaatagac tttaagagg acggaaatat attaggacat         420
aaattagaat ataattataa tagccataat gtatatataa tggcagacaa acaaaaaaat        480
ggaataaaag taaattttaa aataagacat aatatagagg acggaagcgt acaattagca        540
gaccattatc aacaaaatac accaataggt gacggaccag tattattacc agacaatcat        600
tatttaagca cacaaagcgc attaagcaaa gacccaaatg aaaaaagaga ccatatggta        660
ttattagaat ttgtaacagc agcaggaata acattaggaa tggacgaatt atataaataa        720

<210> SEQ ID NO 10
<211> LENGTH: 720
<212> TYPE: DNA
<213> ORGANISM: Homo sapiens

<400> SEQUENCE: 10
atggtgagca agggcgagga gctgttcacc ggggtggtgc ccatcctggt cgagctggac          60
ggcgacgtaa acggccacaa gttcagcgtg tccggcgagg gcgagggcga tgccacctac        120
ggcaagctga ccctgaagtt catctgcacc accggcaagc tgcccgtgcc ctggcccacc        180
ctcgtgacca ccttcaccta cggcgtgcag tgcttcagcc gctaccccga ccacatgaag        240
cagcacgact tcttcaagtc cgccatgccc gaaggctacg tccaggagcg caccatcttc        300
ttcaaggacg acggcaacta caagacccgc gccgaggtga agttcgaggg cgacaccctg        360
gtgaaccgca tcgagctgaa gggcatcgac ttcaaggagg acggcaacat cctggggcac        420
aagctggagt acaactacaa cagccacaac gtctatatca tggccgacaa gcagaagaac        480
ggcatcaagg tgaacttcaa gatccgccac aacatcgagg acggcagcgt gcagctcgcc        540
gaccactacc agcagaacac ccccatcggc gacggccccg tgctgctgcc cgacaaccac        600
```

```
tacctgagca cccagtccgc cctgagcaaa gaccccaacg agaagcgcga tcacatggtc        660
ctgctggagt tcgtgaccgc cgccgggatc actctcggca tggacgagct gtacaagtaa       720
```

We claim:

1. A method for detecting RNA export from the cell nucleus of a eukaryotic target cell, comprising
   (a) providing a polynucleotide which codes for a reporter protein and which further comprises
      (i) a cis-active RNA export signal which is in operative linkage with the polynucleotide
      (ii) a functional 5' splice donor without a 3' splice acceptor,
      (iii) an A/T content that is greater than 50%, which reduces the metabolic stability of a reporter RNA which encodes said reporter protein in the cell nucleus;
   (b) introducing the polynucleotide into the cell nucleus of the target cell so that it is present therein in operative linkage with a transcription control sequence, and that upon transcription of the polynucleotide there is generation of a transcript in which the segment of the transcript coding for the reporter protein cannot be subjected to any efficient splicing process;
   (c) providing a trans-active export factor;
   (d) transcribing the polynucleotide; and
   (e) determining whether the resulting transcript is exported from the cell nucleus.

2. The method according to claim 1, wherein the polynucleotide additionally comprises a choice of codons which is at least partially adapted to the choice of codons of exported viral RNA, leading to a reduction of the metabolic stability of a reporter RNA in the cell nucleus.

3. The method according to claim 1, wherein the polynucleotide additionally comprises a choice of which is at least partially adapted to the choice of codons of HIV-1 (human immunodeficiency virus 1), leading to a reduction of the metabolic stability of a reporter RNA in the cell nucleus.

4. The method according to claim 1, wherein the polynucleotide which codes for the reporter protein is a synthetically produced polynucleotide.

5. The method according to claim 1, wherein the reporter protein is a fluorescent protein.

6. The method according to claim 5, wherein the fluorescent protein is GFP (green fluorescent protein), BFP (blue fluorescent protein), RFP (red fluorescent protein), YFP (yellow fluorescent protein), eGFP (enhanced green fluorescent protein), eBFP (enhanced blue fluorescent protein), eRFP (enhanced red fluorescent protein), eYFP (enhanced yellow fluorescent protein) or hrGFP.

7. The method according to claim 1, wherein the reporter protein comprises a detectable enzymatic activity.

8. The method according to claim 7, wherein the reporter protein is LUC (luciferase), AP (alkaline phosphatase), SEAP (secretory alkaline phosphatase) or CAT (chloramphenicol acetyltransferase).

9. The method according to claim 1, wherein the reporter protein is an immunologically detectable protein.

10. The method according to claim 1, wherein the reporter protein is a selection marker.

11. The method according to claim 1, wherein the reporter protein is encoded by a regulatory gene which regulates the expression of other genes.

12. The method according to claim 1, wherein the polynucleotide comprises a cis-active RNA export element.

13. The method according to claim 12, wherein the cis-active RNA export element is a constitutive RNA export element.

14. The method according to claim 13, wherein the cis-active RNA export element is MPMV CTE (Mason Pfizer monkey virus constitutive transport element), RSV CTE (Rous sarcoma virus constitutive transport element) or SRV CTE (simian retrovirus constitutive transport element).

15. The method according to claim 12, wherein the cis-active RNA export element is an export element which is recognized by a viral export factor.

16. The method according to claim 15, wherein the cis-active RNA export element is HIV-1 RRE (human immunodeficiency virus 1 Rev responsive element), HIV-2 RRE (human immunodeficiency virus 2 Rev responsive element), SIV RRE (simian immunodeficiency virus Rev responsive element), HTLV-I (human T-cell leukemia virus I) Rex responsive element or HTLV-II (human T-cell leukemia virus II) Rex responsive element.

17. The method according to claim 11, wherein the regulatory gene is a transcription factor.

18. The method according to claim 1, comprising employing a viral cis-active RNA export element.

19. The method according to claim 1, wherein the A/T content is increased throughout a reporter construct.

20. The method according to claim 1, wherein the eukaryotic cell is a mammalian cell.

21. A method for detecting RNA export from the cell nucleus of a eukaryotic target cell, comprising
   (a) providing a polynucleotide which codes for a reporter protein and which further comprises
      (i) a cis-active RNA export signal which is in operative linkage with the polynucleotide
      (ii) a functional 5' splice donor without a 3' splice acceptor at 3' from said cis-active RNA export signal
      (iii) an A/T content that is greater than 50%, which reduces the metabolic stability of a reporter RNA which encodes said reporter protein in the cell nucleus;
   (b) introducing the polynucleotide into the cell nucleus of the target cell so that it is present therein in operative linkage with a transcription control sequence, and that upon transcription of the polynucleotide there is generation of a transcript in which the segment of the transcript coding for the reporter protein cannot be subjected to any efficient splicing process;
   (c) providing a trans-active export factor;
   (d) transcribing the polynucleotide; and
   (e) determining whether the resulting transcript is exported from the cell nucleus.

* * * * *